United States Patent [19]

Averback et al.

[11] Patent Number: 6,130,221

[45] Date of Patent: *Oct. 10, 2000

[54] PHARMACEUTICAL AGENTS THAT IMPEDE THE INITIATION AND PROGRESSION OF PRIMARY AND SECONDARY DMS DISRUPTIONS

[75] Inventors: Paul Averback; Hossein Ghanbari, both of Beaconsfield; Iraj Beheshti, Montreal; David Morse, Anjou, all of Canada

[73] Assignee: Nymox Corporation, Dorval, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/858,343

[22] Filed: May 19, 1997

Related U.S. Application Data

[60] Provisional application No. 60/040,194, Mar. 5, 1997.

[51] Int. Cl.[7] ...................... A61K 31/495; C07D 241/04; C07D 295/00
[52] U.S. Cl. .................. 514/255.02; 544/358; 544/380; 544/382; 544/398; 544/403
[58] Field of Search ...................... 514/255.02; 544/358, 544/380, 382, 398, 403

[56] References Cited

U.S. PATENT DOCUMENTS

| | | | |
|---|---|---|---|
| 3,028,428 | 3/1962 | Van Der Stelt | 260/570 |
| 3,060,242 | 10/1962 | Gordon et al. | 260/611 |
| 4,540,564 | 9/1985 | Bodor | 424/9 |
| 4,816,416 | 3/1989 | Averback | 436/166 |
| 4,919,915 | 4/1990 | Averback | 424/7.1 |
| 5,231,170 | 7/1993 | Averback | 530/388.1 |
| 5,280,032 | 1/1994 | Ono et al. | 514/336 |
| 5,567,720 | 10/1996 | Averback | 514/345 |

FOREIGN PATENT DOCUMENTS

| | | |
|---|---|---|
| 0 097 340 A2 | 6/1983 | European Pat. Off. . |
| 0 097 340 | 1/1984 | European Pat. Off. . |
| 0 189 679 | 12/1985 | European Pat. Off. . |
| 0 189 679 | 8/1986 | European Pat. Off. . |

OTHER PUBLICATIONS

H. Morren et al.: "Nouvelles substances antihistaminiques a action prolongee: les 1–4 bis (aralcoyl) piperazines" vol. 60, 1951, pp. 282–295, XP002079758 Oxford GB.
XP–002079758 Morren et. al., Bull. Soc. Chim. Belg., Nouvelles Substances Antihistaminiques a Action Prolongee: les 1–4 bis (aralcoyl) Piperazines, vol. 60 (1951), pp. 282–295.
Averback, "Parasynaptic Corpora Amylacea in the Striatum" *Arch Pathol Lab Med* 105:334–335 (1981).
Averback, "Unusual Particles in Motor Neuron Disease" *Arch Pathol Lab Med* 105:490–493 (1981).
Blessed et al., "The Association Between Quantitative Measures of Dementia and of Senile Change in the Cerebral Grey Matter of Elderly Subjects" *Brit. J. Psychiat* 114:797–811 (1968).
Tomlinson et al., "Observations on the Brains of Non–Demented Old people" *Journal of the Neurological Sciences* 7:331–356, 1968.
Tomlinson et al., "Observations on the Brain of Demented Old People" *Journal of the Neurological Sciences* 11:205–242 (1970).
Corsellis, "Ageing and the Dementias" *Greenfield's Neuropathology* pp. 796–848 (1976).
Averback, "Dense Microspheres in Normal Human Brain" *Acta Neuropathologica* 61:148–152 (1983).
Hara, "Microscopic Globular Bodies in the Human Brain" *Journal of Neuropathology and Experimental Neurology* 45:169–178 (1986).
Kono et al., Is it Useful to Manage Alzheimer's Disease as Two Clinical Subtypes: Early Onset and Late Onset Subtypes? *Basic, Clinical, and Therapeutic Aspects of Alzheimer's and parkinson's* .
Brandt et al., "Relation of Age at Onset and Duration of Illness to Cognitive Functioning in Alzheimer's Disease" *Neuropsychiatry, Neuropsychology, and Behavioral and Behavioral Neurology*, 1989, vol. 2, No. 2, pp. 93–101.
Knesevich et al., "Aphasia, Family History, and the Longitudinal Course of Senile Dementia of the Alzheimer Type" *Psychiatry Research* 14:255–263 (1985).
Wisniewski, Neuritic (Senile) Plaques and Filamentous Changes in Aged Rhesus Monkeys *Journal of Neuropathology and Experimental Neurology* pp. 566–584 (1973).
Selkoe et al., "Conservation of Brain Amyloid Proteins in Aged Mammals and Humans with Alzheimer's Deseade" *Science* 235:873–877, 1987.

*Primary Examiner*—Mukund J. Shah
*Assistant Examiner*—Tamthom N. Truong
*Attorney, Agent, or Firm*—Foley & Lardner

[57] ABSTRACT

Compositions comprising a pharmaceutically effective amount of a compound that impedes disruption of intact dense microspheres (DMS) by acting on DMS either to prevent disruption, or if disrupted, act on pre-disrupted DMS in such a way that, when the composition is administered to a test animal that has received an injection of DMS, it reduces the mean volume of tissue occupied by disrupted DMS, reduces the ratio of the number of inflammatory cells per DMS, or increases the ratio of the number of macrophages containing disrupted DMS per DMS, are useful for treating cerebral amyloidosis. The compound that impedes disruption of intact DMS is represented by the following general Formula (A):

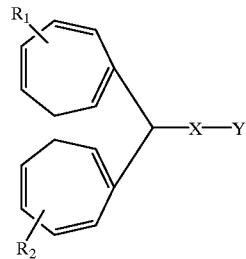

Formula (A)

9 Claims, 13 Drawing Sheets

PHARMACEUTICAL AGENTS THAT IMPEDE THE INITIATION AND PROGRESSION OF PRIMARY AND SECONDARY DMS DISRUPTIONS

This application is based on provisional application Ser. No. 60/040,194 filed Mar. 5, 1997.

BACKGROUND OF THE INVENTION

1. Field of the Invention

The present invention relates to compounds that act, at physiologically-compatible levels, to impede the formation of amyloid in brain, including Alzheimer senile amyloid plaques in vivo. More specifically, the present invention relates to compounds that impede the transformation of dense microspheres (DMS) into amyloid. The invention also relates to methdology for the screening of compounds that possess this activity, and to treating cerebral amyloidosis by administering such compounds therapeutically.

2. Description of Related Art

There is no effective therapy for cerebral amyloidosis, which almost invariably has a fatal outcome following the onset of amyloid deposits. For example, Alzheimer's disease is estimated to be the fourth or fifth leading cause of death in North Americans.

A universally accepted indicator of cerebral amyloidosis is the accumulation of lesions, so-called "senile plaques," that are comprised in large part of amyloid fibrils. Senile plaques are spherical, ranging from 10 to 200 $\mu$m in diameter, and are found occasionally in aged cerebral cortex (see below) but in larger numbers in Alzheimer-affected cortex.

Most specialists agree that reproduction of amyloid fibrils experimentally from precursor materials which are extracted, activated, or otherwise derived from human brain constitutes the best available evidence linking an agent or precursor to the progression of cerebral amyloidosis. Indeed, the literature has documented the use of such materials from human brain, normal and Alzheimer-affected, that are not already amyloid, and their transformation into amyloid.

Accordingly, a reliable indicator is available for compounds that might be effective in treating cerebral amyloidosis. In particular, it is possible to determine whether a given compound prevents the structural tansition of a brain-localized precursor to a β-pleated sheet conformation and thus prevent conversion to cerebral amyloid (i.e., that displays "anti-amyloid activity") at physiologically acceptable levels of the active agent. See U.S. Pat. No. 5,231,170, the contents of which are incorporated by reference.

In a majority of cases, subjects with cerebral amyloidosis, including Alzheimer's patients, display symptoms on a quantitative basis. Blessed et al., *Brit J. Psychiatry* 114: 797–811 (1968); Tomlinson et al., *J. Neurol. Sci.* 7: 331–56 (1968); Tomlinson, B. E., et al., *J. Neurol. Sci.* 11: 205–42 (1970); Corsellis, MENTAL ILLNESS AND THE AGEING BRAIN, Oxford University Press, London (1962); Corsellis, "Ageing and the Dementias," in GREENFIELD'S NEUROPATHOLOGY 796–848, Edward Arnold, London (1976). Elderly subjects who have a small number of senile plaques are asymptomatic and are categorized by some experts as preclinical, by others as presymptomatic, and by still other authorities as normal variants. In any event, the elderly brain apparently can have a low number of senile plaques and still be categorized as "normal." When the amyloid plaque number is high, however, symptoms of dementia appear. Thus, treatment regimens that prevent the formation of amyloid plaques or that reduce the number or rate of formation of amyloid plaques are useful.

A microscopic structure, the so-called "dense microsphere" (DMS), is found in normal brain and in brain affected by Alzheimer's disease. See Averback, *Acta Neuropathol.* 61: 148–52 (1983); results confirmed by Hara, *J. Neuropath. Exp. Neurol.* (1986). Evidence for the existence of dense microspheres comes from microscopic histological section studies of fixed whole brain tissue, where the dense microspheres are seen to have a proteinaceous central region ("DMS protein") surrounded by continuous membrane ("DMS membrane").

The extraction, purification, and characterization of isolated samples of DMS and the use of DMS material have been documented. See, for example, U.S. Pat. Nos. 4,919,915 and 4,816,416, the respective contents of which are incorporated by reference.

DMS disruption is believed to commence after individual DMS reach a threshold size in the elderly or Alzheimer group. Even DMS that have reached the threshold size are quite small, with diameters on the order of approximately 10 microns or less. When the DMS disrupt, constituent protein matter transforms and redistributes to occupy a tissue volume, (anywhere between 10 to 1,000 times larger than the precedent DMS), which comprises a much larger injury focus.

SUMMARY OF THE INVENTION

Preventing the disruption of DMS would prevent the formation of amyloid plaques. If DMS disruption can be curtailed, for example, by around 25% or more, cerebral amyloid formation, and its rate of formation, induced by DMS disruption also can be reduced or prevented. Thus, reducing the size of the injury foci associated with disrupted DMS would impede the formation of anyloid plaques, by reducing the number of DMS disruptions that may be caused by an initial disruption. In addition, reducing the persistence of injury and inflammation associated with DMS disruption, including, for example, increasing the digestion and removal of DMS material through the reticuloendothelial system, would prevent the formation of amyloid plaques or, at least, reduce the number and/or rate of formation of other, secondary DMS disruptions.

Accordingly, a need exists for an approach to preventing DMS disruption. A need also exists for a method to reduce the size of the tissue volume associated with disrupted DMS (injury foci). Furthermore, there is a need for a technique to reduce the persistence of inflammatory reaction brought about by DMS disruption, as well as for methods to increase the digestion and removal of DMS material through the reticuloendothelial system.

It therefore is an object of the present invention to provide a composition and a method that are useful in impeding DMS disruption and, hence, in treating cerebral amyloidosis, a condition characterized by the presence of abnormal amounts of amyloid β-protein associated plaques (senile plaques) and other amyloid deposits. It is an additional object to provide a screening approach for identifying compounds that are useful in impeding DMS disruption.

It is also an object of the present invention to provide a treatment for cerebral amyloidosis by the administration of a compound selected from a class of pharmaceutically active agents that have in common an ability to impede the disruption of intact DMS.

In accomplishing the foregoing objects, a method has been provided, in accordance with one aspect of the present invention, for treating cerebral amyloidosis, comprising the step of administering to a subject in need thereof, a pharmaceutically effective amount of a compound that impedes disruption of intact DMS by: (i) reducing the mean tissue volume of disrupted DMS; (ii) reducing the ratio of the number of inflammatory cells per DMS; or (iii) increasing the ratio of the number of macrophages containing disrupted DMS material per DMS, each when compared to controls. The compound impedes the dirsuption of intact DMS when administered, at an in-tissue concentration of about $10^{-5}$ M or less, to an experimental animal or to a test preparation of human postmortem brain that has received an intracerebral injection of DMS. In one preferred embodiment, the compound thus administered impedes disruption of intact DMS by reducing the mean tissue volume of disrupted DMS material. The compound acts on DMS components in such a way that disrupted DMS in situ attain a significantly reduced diameter, volume of tissue occupied by the redistributed transformed DMS protein material, and associated injury foci, when compared to the diameter, volume of tissue occupied, and injury foci of disrupted DMS in an untreated subject or in a subject treated with an inactive agent.

In accordance with another aspect of the present invention, there is provided a composition for treating cerebral amyloidosis, comprising a pharmaceutically effective amount of a compound that impedes disruption of intact DMS by: (i) reducing the mean tissue volume of disrupted DMS; (ii) reducing the ratio of the number of inflammatory cells per DMS; or (iii) increasing the ratio of the number of macrophages containing disrupted DMS material per DMS, each when compared to controls. The compound impedes the dirsuption of intact DMS when administered, at an in-tissue concentration of about $10^{-5}$ M or less, to an experimental animal or to a test preparation of human postmortem brain that has received an intracerebral injection of DMS. The compositions and methods of using the compositions typically include at least one of the aforementioned compounds in combination with a pharmaceutically acceptable sterile vehicle, as described in REMINGTON'S PHARMACEUTICAL SCIENCES: DRUG RECEPTORS AND RECEPTOR THEORY, (18th ed.), Mack Publishing Co., Easton Pa. (1990).

Compounds also are provided that are effective in reducing the number of subsequent DMS disruptions brought about by an initial DMS disruption by reducing the ratio of the number of inflammatory cells per DMS, i.e., reducing the extent of the injury foci associated with the transformation and redistribution of protein material of an initial disrupted DMS. These compounds, when administered to a test animal that has received an injection of DMS at an in-tissue concentration of about $10^{-5}$ M or less, result in less evidence of inflammatory reaction in relation to persistent DMS materials at the DMS injection site measured, for example, by the number of inflammatory cells such as polymorphonuclear leukocytes and mononuclear leukocytes per DMS in each injury focus, or the tissue volume taken up by non-macrophage inflammatory cells per DMS in each injury focus, when compared to controls at the same time intervals, for instance, at 24 hours and 48 hours, respectively.

In accordance with yet another aspect of the present invention, compounds are provided that are effective in reducing the number of subsequent DMS disruptions brought about by an initial DMS disruption by increasing the ratio of the number of macrophages containing disrupted DMS material per DMS, i.e., promoting the digestion and removal of the DMS material through the reticuloendothelial system. By promoting the digestion and removal of the DMS material, the compounds reduce the extent and duration of the effect of the disrupted DMS and therefore impede subsequent DMS disruptions. These compounds, when administered to a test animal that has received an injection of DMS at an in-tissue concentration of about $10^{-5}$ M or less, result in more evidence of digestion and removal by the reticuloendothelial system, when compared to controls. Digestion and removal can be measured, for example, by the presence of intracellular intact DMS protein material within the cytoplasm of macrophages and mononuclear phagocytes and the numbers thereof at or near the site of DMS disruption, or the presence of intracellular digested, altered, proteolyzed or otherwise transformed DMS protein material within the cytoplasm of macrophages and mononuclear phagocytes and the numbers thereof at or near the site of DMS disruption.

Illustrative of the compounds within the present invention include those of general formula (A):

Formula (A)

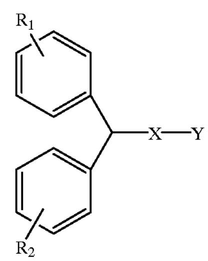

where X is selected from

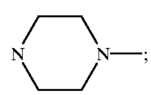

;  ; or $-O-(CH_2)_n-$ and Y is selected from

;  ;

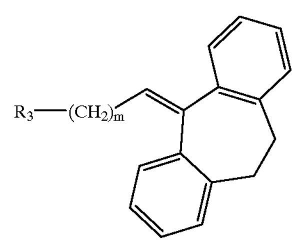

;

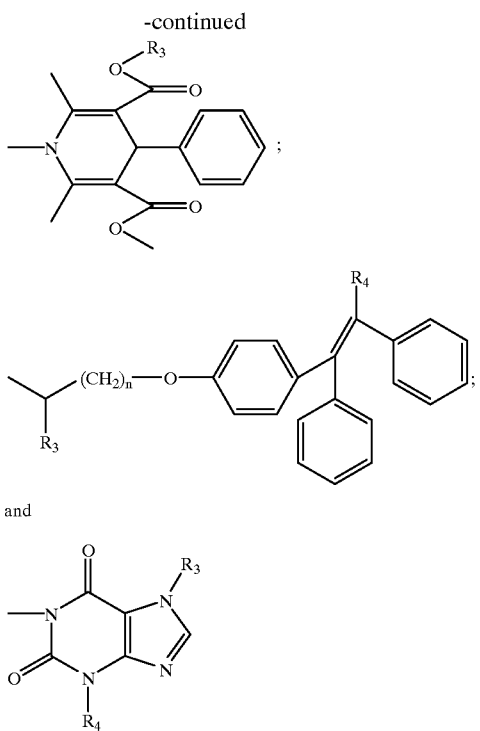

In the general formula (A) above:

R₁ and R₂ are each one or more independent substituents selected from hydrogen, C1–C5 alkyl, C2–C5 alkenyl, C3–C5 cycloalkyl, C1–C5 alkoxy, C2–C5 alkynyl, halogen, C1–C5 alkoxy, C1–C5 haloalkyl, alkylamino, phenyl, nitro, carboxyl, piperazinyl, pyridyl, and fused ring systems; wherein if $R_1$ or $R_2$ are piperazinyl, a nitrogen atom on each piperazinyl may be substituted with a moiety selected from C1–C5 alkyl, C3–C5 cycloalkyl, C1–C5 haloalkyl, substituted or unsubstituted C1–C5 alkylamino; wherein if $R_1$ or $R_2$ are alkylamino, each alkylamino consists of 1 to 5 carbon atoms and the amino group is unsubstituted or mono- or di-substituted with C3–C5 cycloalkyl, C2–C5 alkenyl, C2–C5 alkynyl or C1–C5 alkyl, and if $R_1$ or $R_2$ is a fused ring system, each individual $R_1$ or $R_2$ involved in the fused ring system, together with the phenyl to which it is attached, forms a fused ring system selected from naphthalene, anthracene, acenaphthylene, fluorene, phenalene, phenanthrene, fluoranthene, acephenanthrylene, aceanthrylene, aceanthrylene, isoindole, indole, quinolizine, isoquinoline, phthalazine, quinoxaline, quinoline, phthalazine, quinazoline, and cinnoline, wherein one or more carbon atoms in the fused ring may be replaced with a nitrogen atom and each ring may be saturated or unsaturated, in whole or in part; wherein each ring may be substituted by one or more substituents selected from halogen, C1–C5 alkyl, C2–C5 alkenyl, C2–C5 alkynyl, and C1–C5 haloalkyl;

R₃ is hydrogen, C1–C5 alkyl, C2–C5 alkenyl, C3–C5 cycloalkyl, C2–C5 alkynyl, amino, C1–C5 alkyl-substituted amino, sulfur, oxygen, phenyl, benzyl, naphthyl and anthracenyl; wherein each aromatic ring may be substituted by one or more substituents selected from halogen, C1–C5 alkyl, C2–C5 alkenyl, C2–C5 alkynyl, and C1–C5 haloalkyl;

R₄ is hydrogen, C1–C5 alkyl, C2–C5 alkenyl, C3–C5 cycloalkyl, C2–C5 alkynyl, amino, C1–C5 alkyl-substituted amino, C1–C5 alkylamino, C2–C5 alkenylamino, C1–C5 alkyl substituted C1–C5 alkylamino, C1–C5 alkyl substituted C2–C5 alkenylamino, sulfur, oxygen, phenyl, benzyl, naphthyl and anthracenyl; wherein each aromatic ring may be substituted by one or more substituents selected from halogen, C1–C5 alkyl, C2–C5 alkenyl, C2–C5 alkynyl, and C1–C5 haloalkyl;

R₅ is nitrogen or carbon;

R₆ and R₇ are each one or more independent substitutions selected from hydrogen, C1–C5 alkyl, C2–C5 alkenyl, C3–C5 cycloalkyl, C1–C5 alkoxy, C2–C5 alkynyl, halogen, C1–C5 haloalkyl, alkylamino, phenyl, nitro, carboxyl, piperazinyl, pyridyl, and fused ring systems; wherein if $R_6$ or $R_7$ is piperazinyl, a nitrogen atom on each piperazinyl may be substituted with a moiety selected from C1–C5 alkyl, C3–C5 cycloalkyl, C1–C5 haloalkyl, substituted or unsubstituted C1–C5 alkylamino; wherein if $R_6$ or $R_7$ is alkylamino, each alkylamino consists of 1 to 5 carbon atoms and the amino group is unsubstituted or mono- or di-substituted with C3–C5 cycloalkyl, C2–C5 alkenyl, C2–C5 alkynyl or C1–C5 alkyl, and if $R_6$ or $R_7$ is a fused ring system, each individual $R_6$ and $R_7$ involved in the fused ring system, together with the phenyl to which it is attached, forms a fused ring system selected from naphthalene, anthracene, acenaphthylene, fluorene, phenalene, phenanthrene, fluoranthene, acephenanthrylene, aceanthrylene, aceanthrylene, isoindole, indole, quinolizine, isoquinoline, phthalazine, quinoxaline, quinoline, phthalazine, quinazoline, and cinnoline, wherein one or more carbon atoms in the fused ring may be replaced with a nitrogen atom and each ring may be saturated or unsaturated, in whole or in part; wherein each ring may be substituted by one or more substituents selected from halogen, C1–C5 alkyl, C2–C5 alkenyl, C2–C5 alkynyl, and C1–C5 haloalkyl;

n is an integer of from 0 to 5;

m is an integer of from 0 to 5;

or a pharmaceutically acceptable salt of such compound.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. Unless otherwise specified, the respective contents of documents cited in the following description are hereby incorporated by reference.

BRIEF DESCRIPTION OF THE DRAWINGS

FIG. 1 illustrates five nerve fibers (lines and triangles) with five individual DMS (black circles), one on each fiber.

FIG. 2 illustrates the initiation of a DMS disruption on one of the five nerve fibers.

FIG. 3 illustrates continued disruption of the disrupted DMS of FIG. 2, and the inducement of disruption of a DMS on an adjacent fiber.

FIG. 4 illustrates a fully disrupted DMS from FIG. 2, and the initiation of disruption of the DMS on the adjacent fiber of FIG. 3.

FIG. 5 illustrates continued disruption of the disrupted DMS of FIG. 4, and the inducement of disruption of a DMS on an adjacent fiber.

FIG. 6 illustrates a fully disrupted DMS from FIG. 4, and the initiation of disruption of the DMS on the adjacent fiber of FIG. 5.

FIG. 7 illustrates continued disruption of the disrupted DMS of FIG. 6, and the inducement of disruption of a DMS on an adjacent fiber.

FIG. 8 illustrates a fully disrupted DMS from FIG. 6, and the initiation of disruption of the DMS on the adjacent fiber of FIG. 7.

FIG. 9 illustrates continued disruption of the disrupted DMS of FIG. 7, and the inducement of disruption of a DMS on an adjacent fiber.

FIG. 10 illustrates a fully disrupted DMS from FIG. 8, and the initiation of disruption of the DMS on the adjacent fiber of FIG. 9.

FIG. 11 illustrates continued disruption of the disrupted DMS of FIG. 10.

FIG. 12 illustrates fully disrupted DMS on all 5 fibers.

FIG. 13 illustrates nerve fibers with one undisrupted DMS in the center, wherein some of the nerve fibers contain undisrupted DMS.

FIG. 14 illustrates the same nerve fibers with the DMS in the center beginning to disrupt.

FIG. 15 illustrates the same nerve fibers with the DMS in the center continuing to disrupt and attaining a disrupted volume where it is now in the region of an adjacent nerve fiber which contains one undisrupted DMS.

FIG. 16 illustrates the same nerve fibers whereby the undisrupted DMS on the adjacent nerve fiber has begun to disrupt.

FIG. 17 illustrates a continuation of the disruption of the DMS on the adjacent nerve fiber of FIG. 16.

FIG. 18 illustrates a continuation of the disruption of the DMS on the adjacent nerve fiber of FIG. 17.

FIG. 19 illustrates the same initial nerve fibers whereby the DMS in the center has disrupted to a greater extent than in FIGS. 14 and 15, and has now impinged on two additional adjacent nerve fibers, each containing one undisrupted DMS.

FIG. 20 illustrates the undisrupted DMS on the adjacent nerve fibers of FIG. 19 beginning to disrupt.

FIG. 21 illustrates a continuation of the disruption of the DMS of FIG. 20.

FIG. 22 illustrates a continuation of the disruption of the DMS of FIG. 21.

FIG. 23 illustrates the center DMS disrupting to an even greater extent than in FIGS. 14, 15 and 19, and impinging on 8 adjacent DMS-containing nerve fibers.

FIG. 24 illustrates many undisrupted DMS on the adjacent nerve fibers of FIG. 23 beginning to disrupt.

FIG. 25 illustrates a continuation of the disruption of the many DMS of FIG. 24.

FIG. 26 illustrates a continuation of the disruption of the many DMS of FIG. 25.

DETAILED DESCRIPTION OF THE PREFERRED EMBODIMENTS

Figure 1:
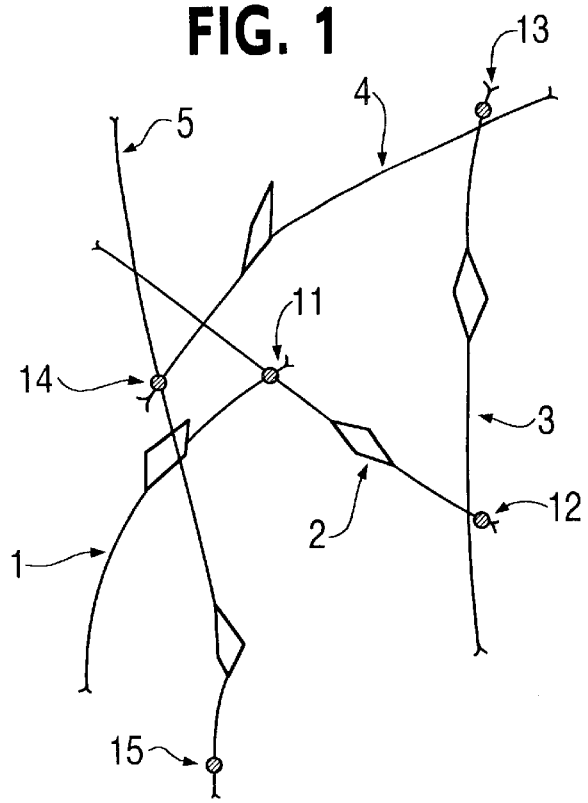
FIGS. 1–12 illustrate schematically DMS disruption and stimulation of subsequent DMS disruption of other DMS on nerve fibers which are associated with the region of the disrupted DMS.

It has been discovered that the development of amyloid fibrils associated, for example, with the evolution of cerebral amyloidosis is tied to the unchecked disruption of DMS in vivo. The connection between DMS disruption and amyloid formation is evidenced by the fact that disrupted DMS treated with Congo Red stain display a red-green congophilic birefringence identical to that found in senile-plaque amyloid. Thus, the most significant aspect of brain damage that characterizes cerebral amyloidosis can be reproduced using material derived, pursuant to the present invention, from normal mammalian brain samples.

A hitherto unrecognized aspect of cerebral amyloid plaque formation by DMS transformation and/or disruption concerns the initiation of the underlying DMS disruption. An important mechanism of initiation and promotion of DMS disruption has been discovered that involves a distinctive autocatalytic phenomenon, whereby the disruption, degeneration, and evolution of an individual DMS into an individual cerebral amyloid plaque provides the stimulus for a group or field of other DMS to disrupt, degenerate and evolve in a recurring set of waves (see FIGS. 1–12). This unchecked, autocatalytic phenomenon causes an exponential growth pattern: small, perhaps statistically insignificant differences (between individual brains) in starting numbers of disrupted DMS in situ evolve into statistically significant differences after generations of the cycle. For example, if all other factors were equal, a subject having an initial group of 100 DMS would not be statistically or symptomatically different from a second subject having an initial group of 98 DMS. However, if over time each of the initial DMS initiated 10 subsequent DMS to disrupt, each of which in turn initiated 10 subsequent DMS disruptions, then group 1 after 20 generations would have $2 \times 10^{20}$ more disrupted DMS than group 2, which is significant.

The compounds of the present invention impede DMS disruption by previously unknown mechanisms that reduce the number of subsequent DMS disruptions brought about by an initial DMS disruption and hence, reduce the cerebral amyloid burden and formation of amyloid plaques. The compounds of the present invention therefore impede disruption of DMS by: (i) reducing the mean volume of tissue occupied by disrupted DMS (i.e., redistributed transformed DMS protein material and the associated injury foci); (ii) reducing the ratio of the number of inflammatory cells per DMS (i.e., persistence of injury and inflammation associated with the disrupted DMS); or (iii) increasing the ratio of the number of macrophages containing disrupted DMS material per DMS (i.e., digestion and removal of DMS material through the reticuloendothelial system). Additionally, a compound of the present invention may prevent the intitial DMS disruption and, hence, prevent any subsequent DMS disruptions.

The usefulness of precluding (inhibiting) cerebral amyloid formation is recognized, and the usefulness of blocking the transformation of cerebral amyloid precursors into amyloid is evident (known as "blocker therapy"). In accordance with blocker therapy, DMS transformation into amyloid plaques is interrupted or inhibited after DMS disruption has occurred. By contrast, the present invention comprehends a therapy, leading to less DMS-derived cerebral amyloid by impeding DMS disruption and/or altering the disruption process by acting on the DMS prior to disruption in such a manner that either prevents disruption, or, when disrupted, reduces subsequent DMS disruptions. Compounds that are effective in blocking DMS transformation in accordance with blocker therapy do not necessarily impede DMS disruption or alter the disruption process by acting on the DMS prior to disruption in the manners described herein, and vice versa.

In accordance with the present invention, if the mean volume of tissue occupied by the disrupted DMS is reduced when compared to the volume of tissue occupied by disrupted DMS in a control subject, the volume of the disrupted DMS preferably is reduced by greater than 10%, more preferably greater than 20%, and most preferably, greater than 30%. (The expression "control subject" in this context denotes either an untreated subject or a subject that has been treated with an inactive placebo.) If the ratio of number of acute inflammatory cells per DMS is reduced when compared to the ratio in a control subject, the ratio is reduced by greater than 10%, preferably 50% and more preferably 100%. In addition, if the ratio of the number of macrophage containing disrupted DMS material per DMS is increased when compared to the ratio in a control subject, the ratio is increased by greater than 10%, preferably greater than 50% and more preferably greater than 100%.

FIGS. 1–12 illustrate how the disruption of one DMS can stimulate subsequent disruption of other DMS on nerve fibers which contact fully disrupted DMS. This phenomenon is addressed by the expressions "subsequent DMS disruptions brought about by an initial DMS disruption," "DMS disruptions brought about by an initial DMS disruption, " and "the autocatalytic phenomenon," respectively. See also FIGS. 13–26, which are discussed in greater detail below.

Figure 2:
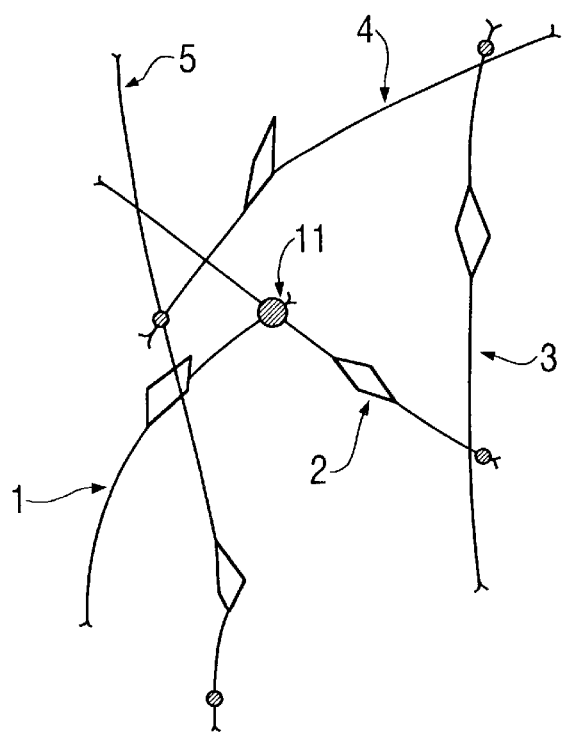

FIG. 1 illustrates five nerve fibers (lines and triangles) with five individual DMS (black circles), one on each fiber, whereby nerve fiber 1 contains undisrupted and intact DMS 11, fiber 2 contains DMS 12, fiber 3 contains DMS 13, fiber 4 contains DMS 14 and fiber 5 contains DMS15. FIG. 2 shows the initiation of disruption of DMS 11 on fiber 1.

Figure 3:
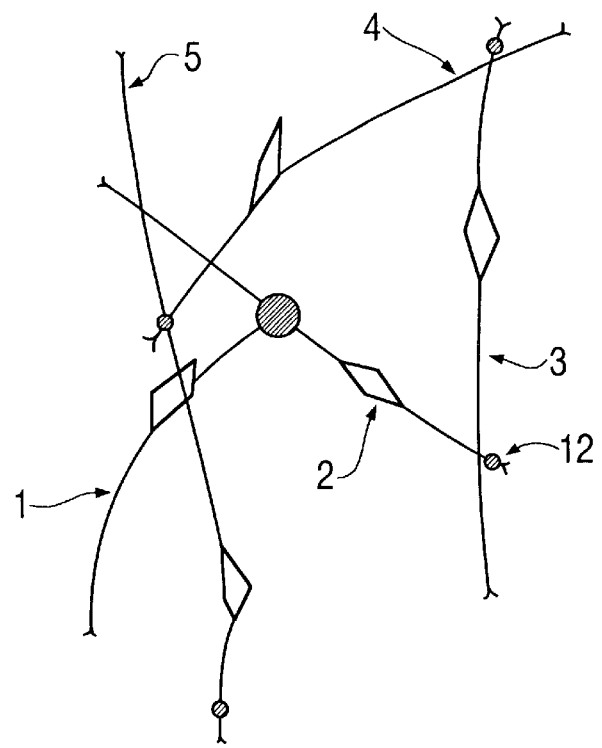

As shown in FIG. 3, DMS 11 of FIG. 2 which had begun to disrupt, continues disrupting and reaches a size which induces disruption of DMS 12 on adjacent fiber 2. If the DMS could be prevented from ever disrupting, or the disruption mechanism altered to an extent which would: (i) prevent the disrupted DMS from attaining a size sufficient to induce subsequent DMS disruptions; (ii) reduce the persistence of injury and inflammation associated with the disrupted DMS which would prevent subsequent DMS disruptions; or (iii) increase the digestion and removal of DMS material through the reticuloendothelial system which also prevents subsequent DMS disruptions, then the autocatalytic phenomenon that is illustrated in FIGS. 1–12 could be prevented.

Figure 4:
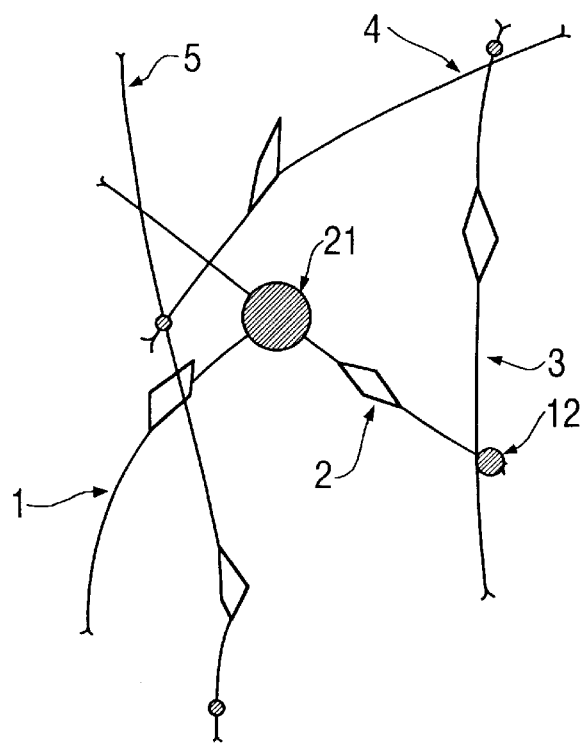
Figure 5:
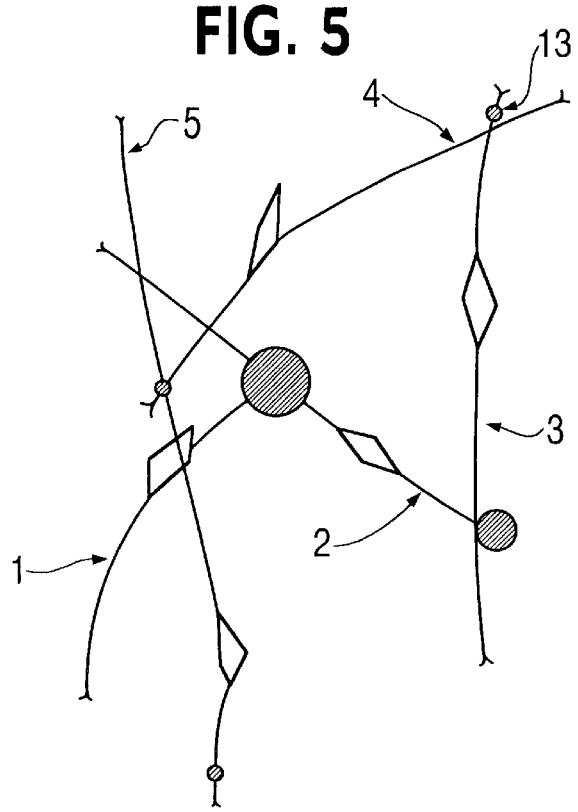
Figure 6:
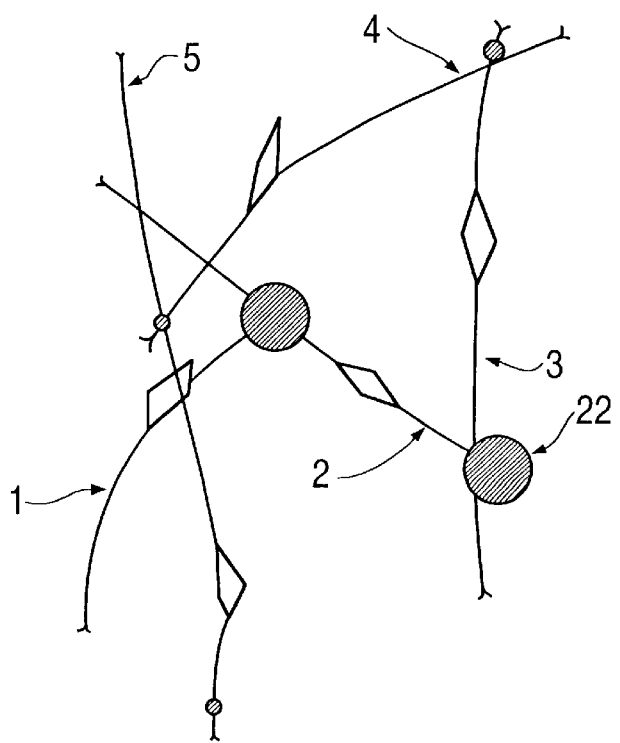
Figure 7:
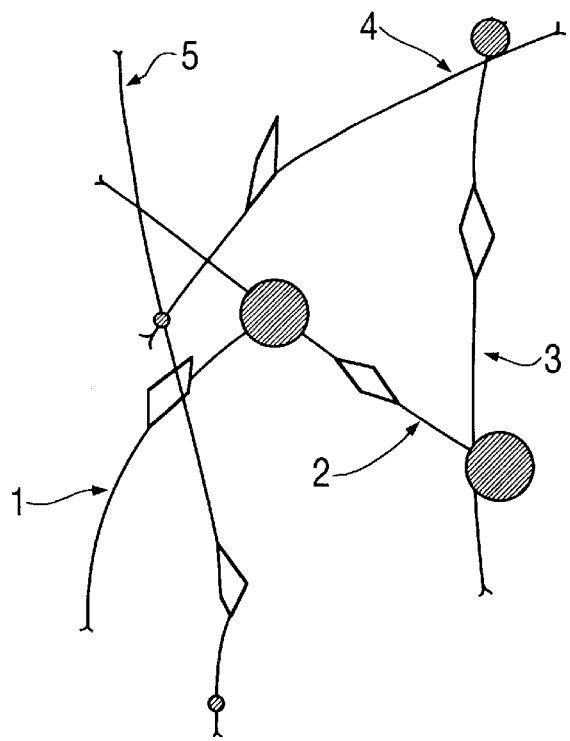
Figure 8:
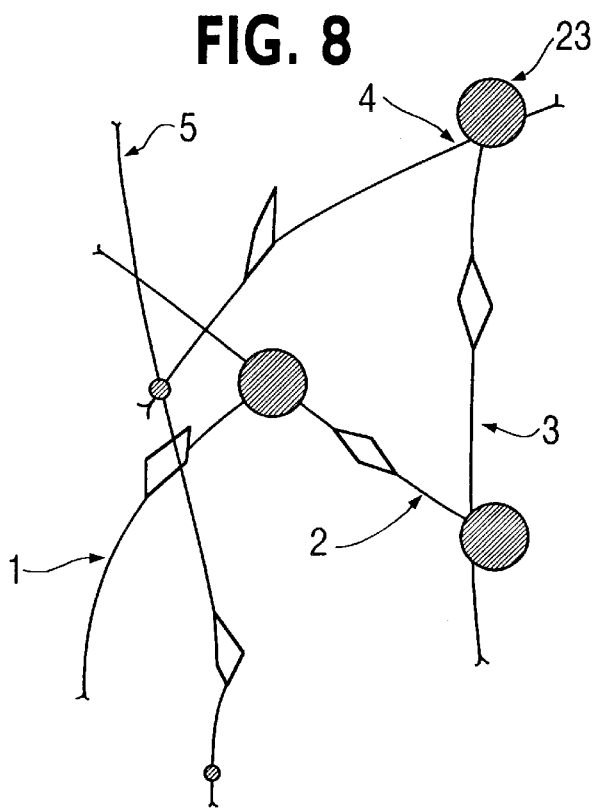
Figure 9:
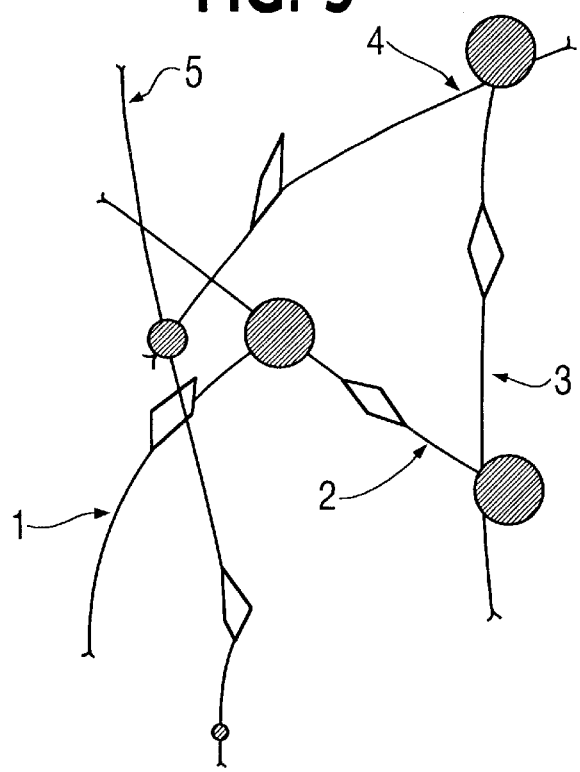
Figure 10:
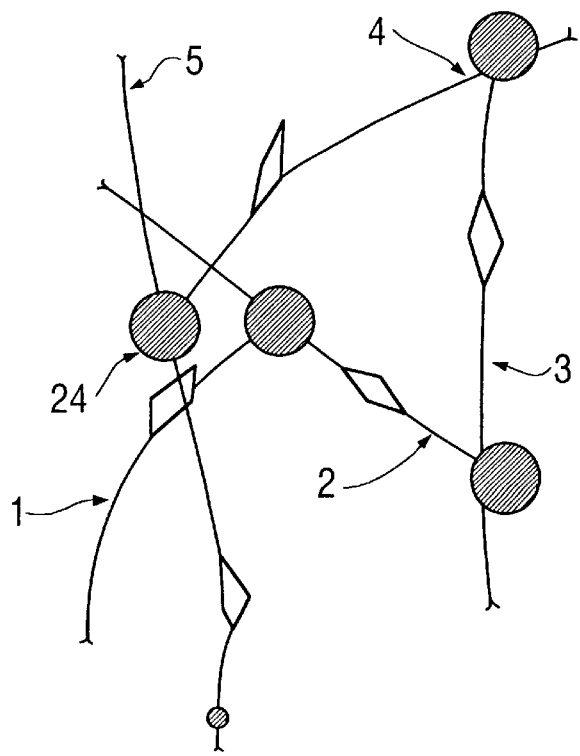
Figure 11:
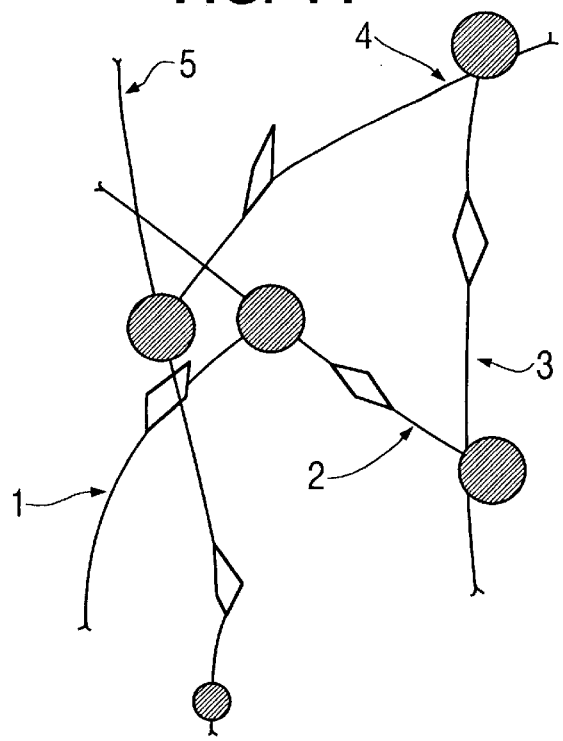
Figure 12:
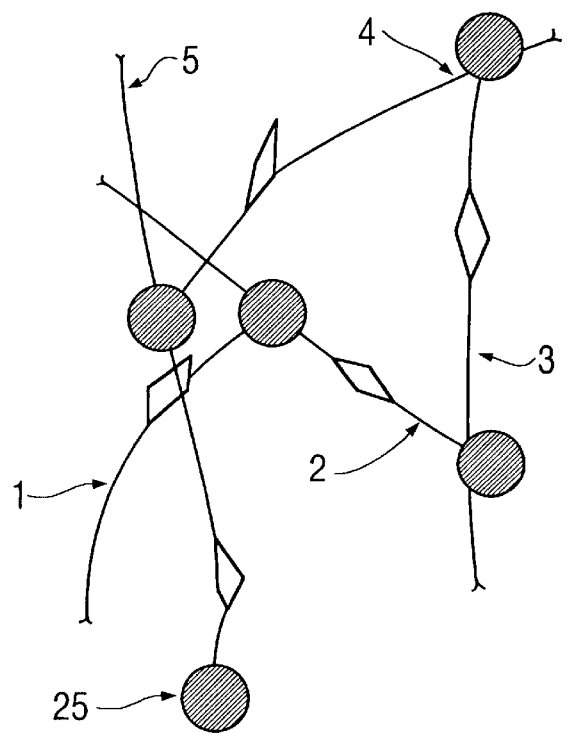

FIG. 4 illustrates the DMS from FIG. 2, now fully disrupted to form disrupted DMS 21, and the initiation of disruption of DMS 12 on adjacent fiber 2 of FIG. 3. As shown in FIG. 5, DMS 12 of FIG. 4, which began disruption, continues to disrupt, and begins to induce disruption of DMS 13 on adjacent fiber 3. This process is repeated for the remaining fibers as shown in FIGS. 6–12. FIG. 6 shows disrupted DMS 22, FIG. 8 shows disrupted DMS 23 on fiber 3, FIG. 10 shows disrupted DMS 24 on fiber 4, and FIG. 12 shows disrupted DMS 25 on fiber 5. As mentioned above, disrupted DMS 21, 22, 23, 24 and 25 result in the formation of cerebral amyloid plaque. Based on the teachings herein, those skilled in the art will appreciate that significant reductions in the size and amount of cerebral amyloid plaque formation can be achieved if the initial DMS disruption were prevented (i.e., prevent the disruption of DMS 11 to disrupted DMS 21), or any subsequent DMS disruption were prevented (DMS 12 into disrupted DMS 22, DMS 13 into disrupted DMS 23, etc.), or if the mechanism of DMS disruption altered so that the resulting disrupted DMS initiate less subsequent DMS disruptions when compared to disrupted DMS in control subjects. Hence, the method of the present invention is effective in treating cerebral amyloidosis, including Alzheimer's disease, because the compounds of the invention, when administered, either (a) inhibit DMS disruption, or (b) alter the DMS disruption process in such a manner that subsequent DMS disruptions are prevented or reduced.

Figure 13:
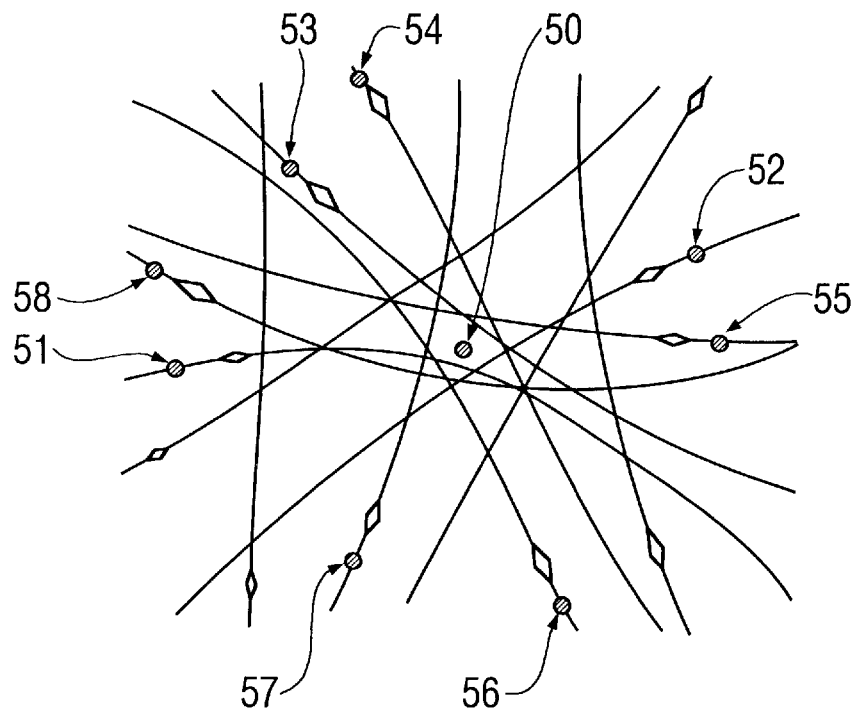
FIGS. 13–26 illustrate how disruption of one DMS can stimulate and bring about the disruption of numerous DMS.

FIGS. 13–26 illustrate how one single DMS 50 can stimulate the growth and disruption of 8 more DMS (51, 52, 53, 54, 55, 56, 57, 58) and, therefore, illustrate the autocatalytic phenomenon brought about by the growth and disruption of DMS in brain. FIG. 13 shows one intact and undisrupted DMS 50 in the center with about 12 nerve fibers in the near vicinity, which contain 8 other DMS (51, 52, 53, 54, 55, 56, 57, 58). The small round objects are intact and undisrupted DMS, the lines are nerve fibers and the empty triangles signify nerve cell bodies. In FIG. 13, DMS 50, and the remaining DMS (51, 52, 53, 54, 55, 56, 57, 58) are stable.

Figure 14:
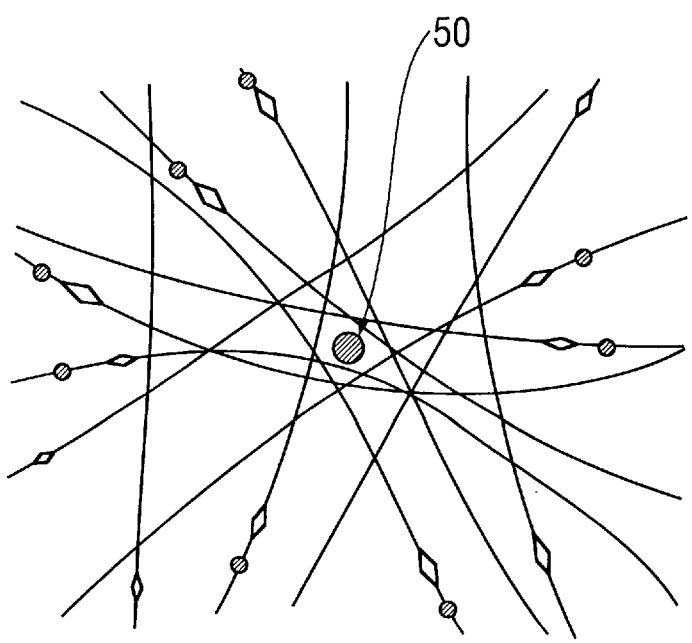
Figure 15:
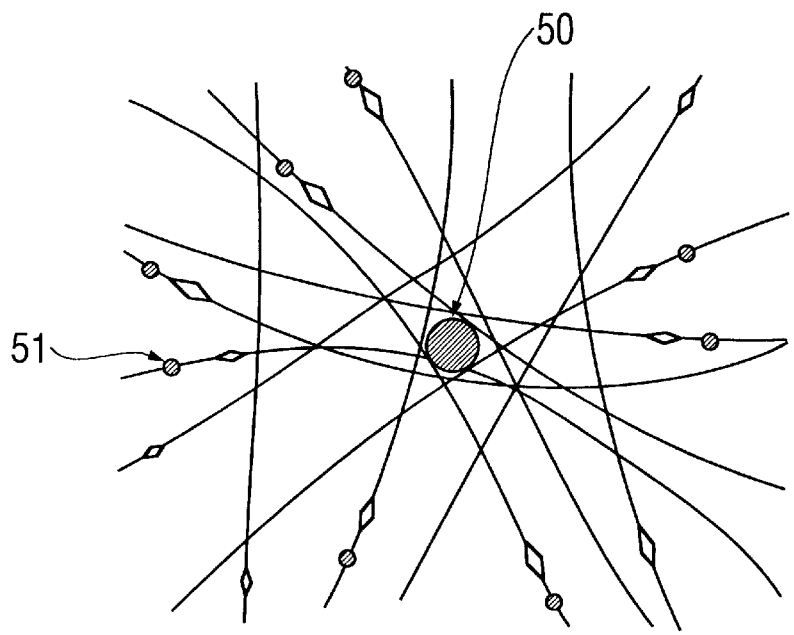
Figure 16:
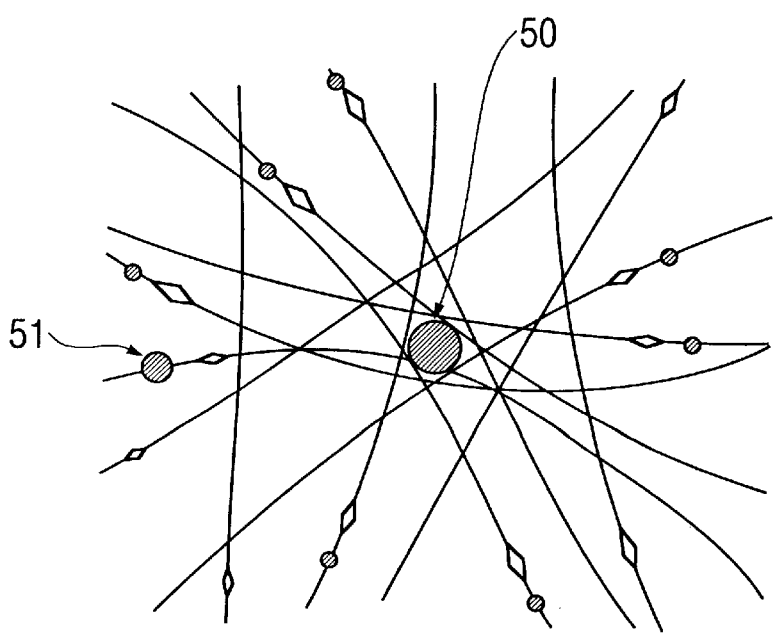
Figure 17:
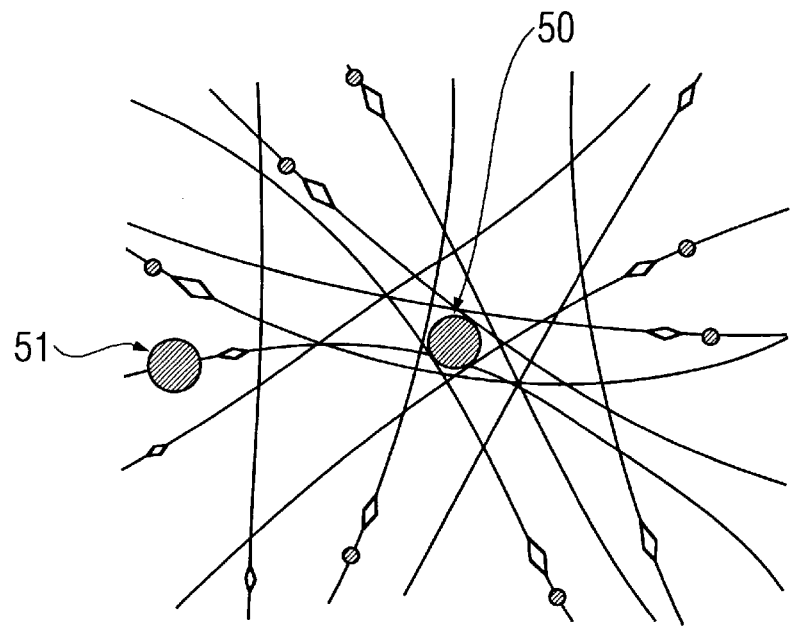
Figure 18:
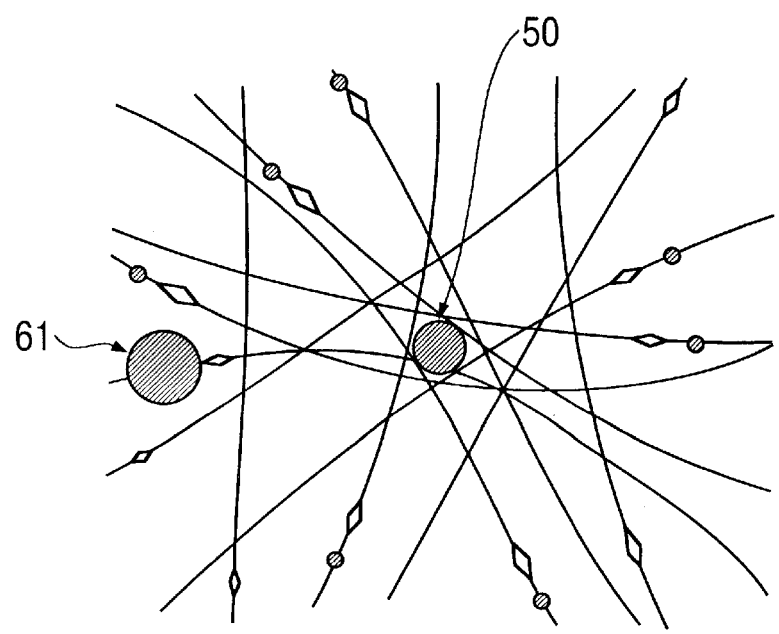
Figure 19:
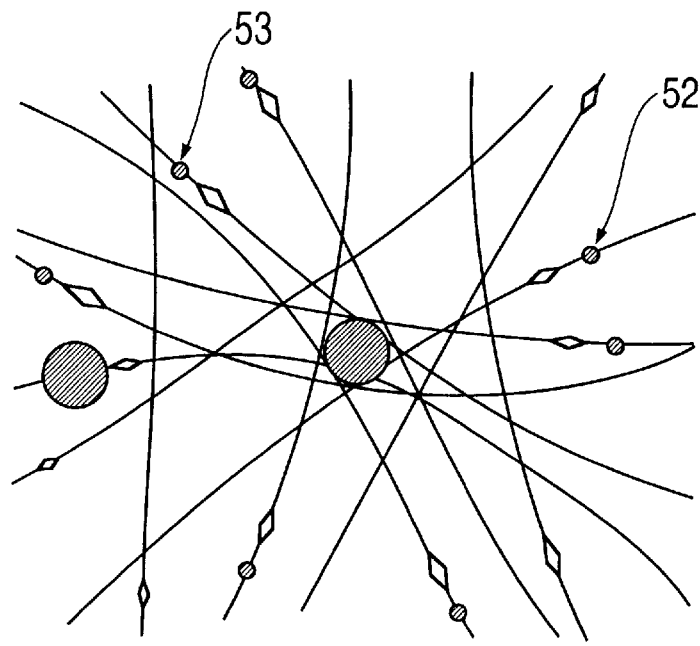
Figure 20:
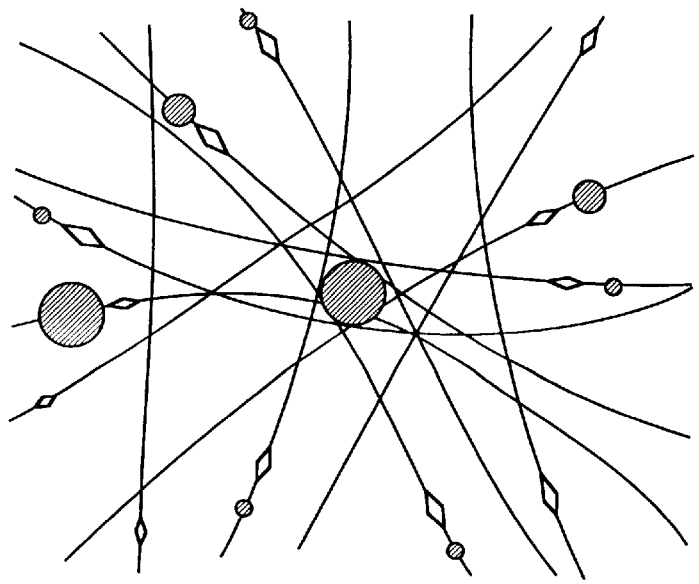
Figure 21:
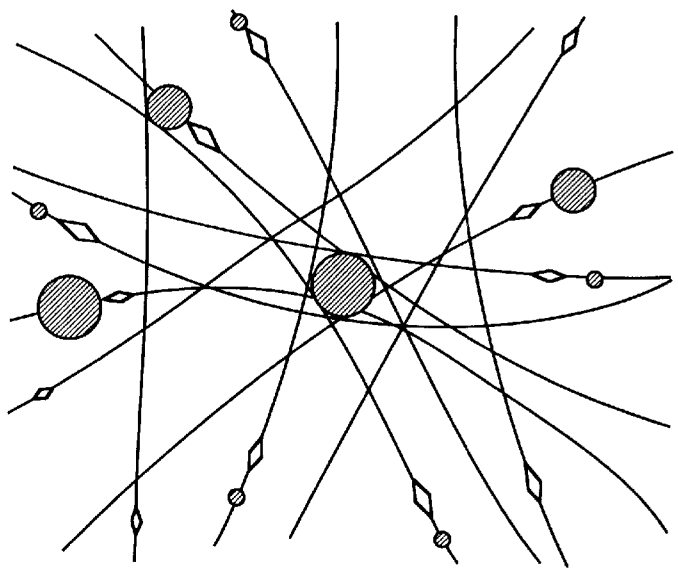
Figure 22:
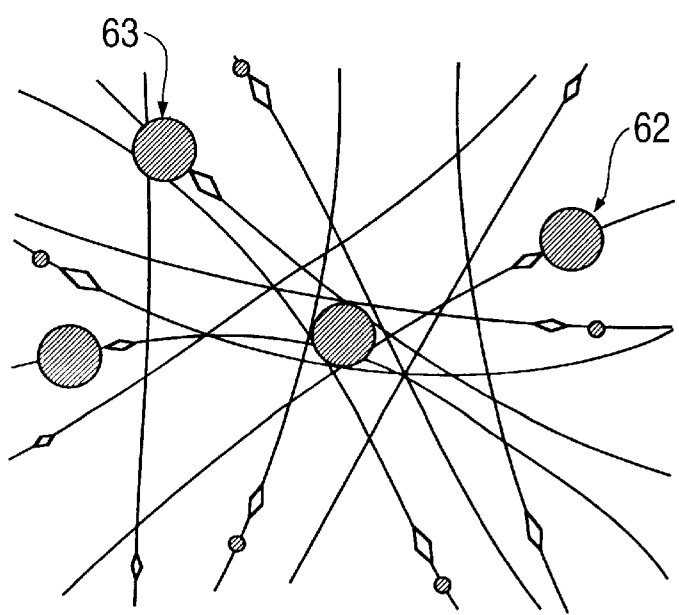

As shown in FIG. 14, DMS 50 is beginning to disrupt and in FIG. 15, it has disrupted to the extent that the disrupted region is impinging on a nerve fiber that contains another DMS 51. In FIGS. 16, 17 and 18, this second DMS 51 begins to disrupt and the transformed redistributed disrupted DMS region enlarges to form fully disrupted DMS 61. In FIG. 19, DMS 50 has disrupted to a greater extent than in FIG. 15 and thus impinges on two (2) additional DMS containing nerve fibers containing DMS 52, 53, such that these DMS, in FIGS. 20, 21 and 22, subsequently disrupt to form disrupted DMS 62 and 63, respectively.

Figure 23:
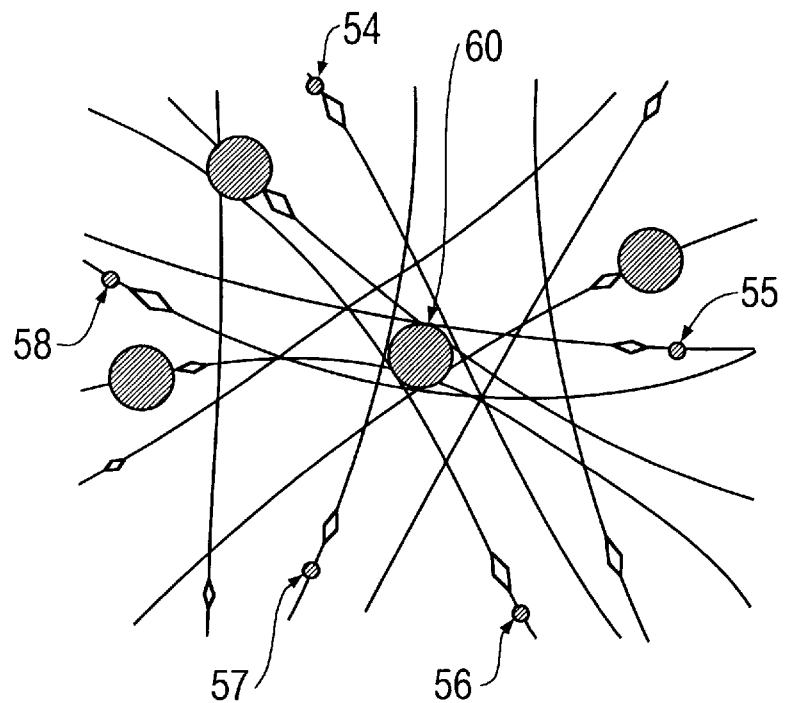
Figure 24:
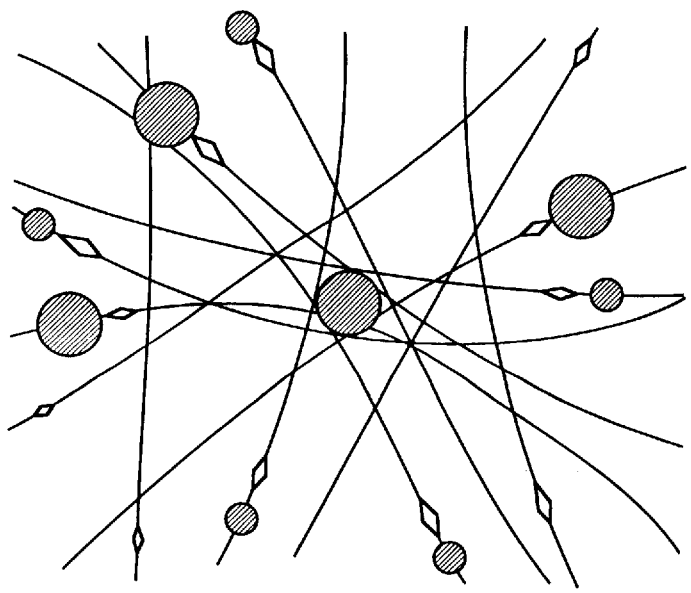
Figure 25:
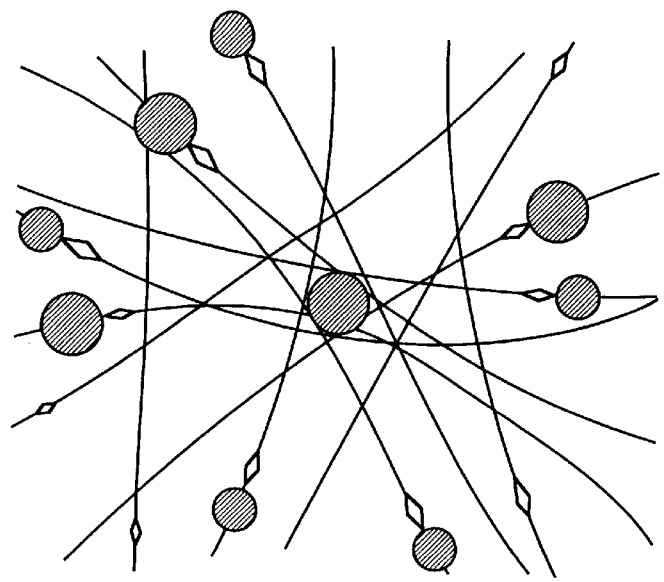
Figure 26:
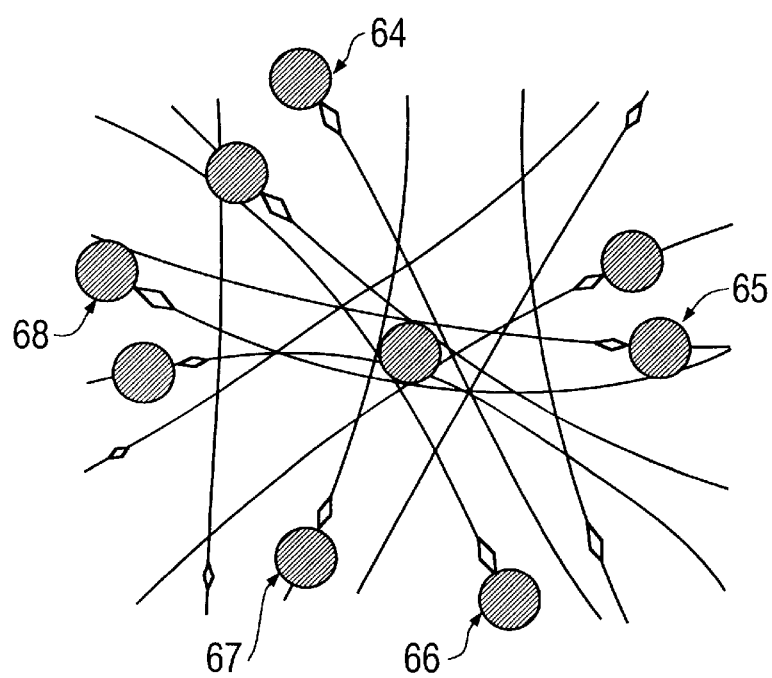

As shown in FIG. 23, the central DMS (originally DMS 50) now has disrupted to an even greater extent to form disrupted DMS 60, and impinges on all DMS containing nerve fibers in the vicinity such that the DMS 54, 55, 56, 57 and 58 in these fibers, in FIGS. 24, 25 and 26 subsequently disrupt to form disrupted DMS 64, 65, 66, 67 and 68, respectively. A comparison of the DMS in FIGS. 15, 19 and 23 shows that a small disruption (FIG. 15) of DMS 50 results in a total of only one secondary disruption (DMS 51 disrupts to form disrupted DMS 61); a larger disruption (FIG. 19) of DMS 50 results in a total of three secondary disruptions (DMS 51 to disrupted DMS 61, DMS 52 into disrupted DMS 62 and DMS 53 into disrupted DMS 63); and the largest disruption (FIG. 13) to form disrupted DMS 60 resulted in a total of eight secondary disruptions. The geometric progression of subsequent DMS disruption is readily apparent when the eight secondary disruptions each individually cause eight more disruptions for a total of 64, and then those 64 each cause eight more for a total of 512 disruptions, and so on.

The newly discovered mechanism, whereby an initial DMS disruption facilitates subsequent DMS disruptions elsewhere (on other nerve fibers, etc.) through an autocatalytic phenomenon, also implicates a phenomenon of senile amyloid-plaque formation leading to the formation of other senile amyloid plaques. The connection between de novo DMS disruption and DMS disruption elsewhere in the brain is evidenced, for example, by observations that:

A. Intact DMS are found within tiny nerve fibers and endings, and the latter are injured by the thousands when a DMS is disrupted and the ensuing injury reaction proceeds to form its associated injury foci of cerebral senile plaque lesions. An initial disrupted DMS injury to a fiber that contains a subsequent DMS at a different location from the initial disrupted DMS explains the initiation of the subsequent DMS disruption. This is illustrated in FIGS. 1 to 12.

B. Initial DMS disruption leading to subsequent DMS disruption through the autocatalytic phenomenon resulting in exponentially greater numbers of disrupted DMS implies an accelerated course of senile plaque progression in comparatively younger subjects where nerve fiber density per unit volume is greater than in comparatively more elderly subjects. In other words, if there are more fibers per unit volume, then more fibers will pass through an area of disruption, or injury foci. Thus, these fibers that pass through the injury foci, and contain intact DMS, will be injured and as a consequence, more DMS disruptions will result. It has been found in some studies that younger cases of cerebral amyloidosis or Alzheimer's disease run a more aggressive, faster course. Kono et al., BASIC, CLINICAL AND THERAPEUTIC ASPECTS OF ALZHEIMER'S AND PARKINSON'S DISEASES, Vol. 2, Plenum Press, N.Y., 143–146; Brandt, et al., *Neuropsychiatr. Neuropsychol. Behav. Neurol.*, 2(2): 93–101 (1989); Knesivich, et al., Psych. Res., 14: 255–263 (1984).

C. The total number of disrupted plus intact DMS in Alzheimer's disease brain has not been found to be significantly higher than in normal controls, but there obviously are greater numbers of disrupted DMS in Alzheimer's disease brain. Averback, *Neurology*, 32(2): A227, (1982). The autocatalytic phenomenon accounts simultaneously for: a) more numbers of disrupted DMS in disease compared to controls; b) the absence of a statistically significant difference in starting material quantity (numbers of intact DMS); and c) the sum of intact plus disrupted DMS being equal in Alzheimer's disease and normal individuals. In other words, Alzheimer's disease individuals and normal individuals start with roughly equal numbers of DMS, but the former group have a higher (faster) rate of transformation to disrupted DMS due to the autocatalytic phenomenon whereby an initial DMS disruption causes subsequent DMS disruptions, and so on.

Treatments that will reduce the number of starting DMS, inhibit the growth of DMS, or alternatively that will delay the time of initiation of the process of DMS disruption, will therefore impede the kinetics of the autocatalytic phenomenon. Delay of the initiation can be achieved by (1) delaying the start of the whole process, for example, by inhibiting the growth of DMS, or (2) by delaying an individual DMS disruption. Retardation of the autocatalytic phenomenon also can be effected by reducing the number of subsequent DMS disruptions brought about by an initial DMS disruption. Throughout this description, the expression "reduce the number and/or rate of subsequent DMS disruptions" denotes a process whereby a given DMS (i) does not disrupt, (ii) disrupts to a lesser extent (i.e., smaller injury foci), (iii) disrupts but reduces the inflammatory reaction in relation to persistent DMS materials, or (iv) disrupts but increases the digestion and removal of the disrupted DMS material. Thus, the overall number of subsequent DMS disruptions will be reduced in accordance with the present invention. A treatment that produces a small, perhaps insignificant, reduction in subsequent DMS disruptions per cycle will, as described above, produce in this exponential process a huge and important reduction in quantities of DMS disruption. This result is that the individual so treated can shift from a high quantity group to a low quantity group and thereby remain asymptomatic, or have fewer symptoms, or have slower progressing symptoms. Quantitative reduction of subsequent DMS disruptions implies that certain individual DMS will have delay of onset of disruption, will not disrupt at all or that disruption will be altered to produce disrupted DMS that do not initiate, or initiate to a lesser extent, further disruptions.

The extent of subsequent DMS disruptions brought about by an initial DMS disruption and brain injury process is proportional to the number of DMS containing fibers that are injured by the initial DMS disruption. For example, in an individual with Alzheimer's disease, a large hippocampal cortical senile plaque can have an injury focus with a diameter of about 100 micrometers and a volume of about 525,000 cubic microns. The plaque effects the injury of thousands of fibers which pass through this volume. If the diameter of the injury focus was reduced to about 80 micrometers, with a corresponding volume of about 268,200 cubic microns and many fewer injured fibers, then the number of subsequent DMS disruptions would be reduced by approximately one-half, because the volume has been halved.

Thus, reducing the diameter of the disrupted DMS by only 20% results in the first instance in a 50% reduction in subsequent DMS disruption. By virtue of the newly discovered autocatalytic phenomenon, this reduction ultimately results in significantly less DMS disruptions overall. A modest diameter reduction in disrupted DMS thereby occasions, at a given point in time, a shift from a high to a low quantity of cerebral amyloid plaques, preventing the subject from becoming symptomatic at that time (see FIGS. 13–26).

Compounds that are effective in reducing the quantity or volume of initial disrupted DMS and, hence, the quantity and volume of disrupted DMS injury foci, can be used to treat cerebral amyloidosis, including Alzheimer's disease. Particularly effective in this regard are compounds that act on DMS protein components or DMS membrane, for example, via intracellular or extracellular binding, so as to limit initial DMS disruption by either preventing DMS disruption altogether or by altering the initial DMS prior to disruption in such a manner that, when disrupted, subsequent DMS disruption is curtailed. Compounds of the present invention are capable of reducing subsequent DMS disruptions brought about by an initial DMS disruption by (i) decreasing the mean tissue volume of disrupted DMS, (ii) reducing the ratio of number of inflammatory cells per DMS, or (iii) increasing the ratio of the number of macrophages containing disrupted DMS material per DMS, i.e., increasing the digestion and removal of the disrupted DMS material through the reticuloendothelial system.

Compounds found to be effective in either preventing DMS disruption or altering pre-disrupted DMS in any of the manners described above can be represented by the general formula (A):

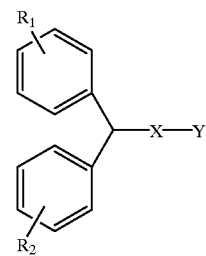

Formula (A)

where X is selected from

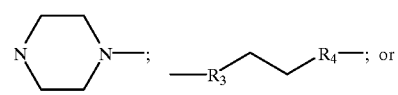

-continued

—O—(CH$_2$)$_n$— and Y is selected from

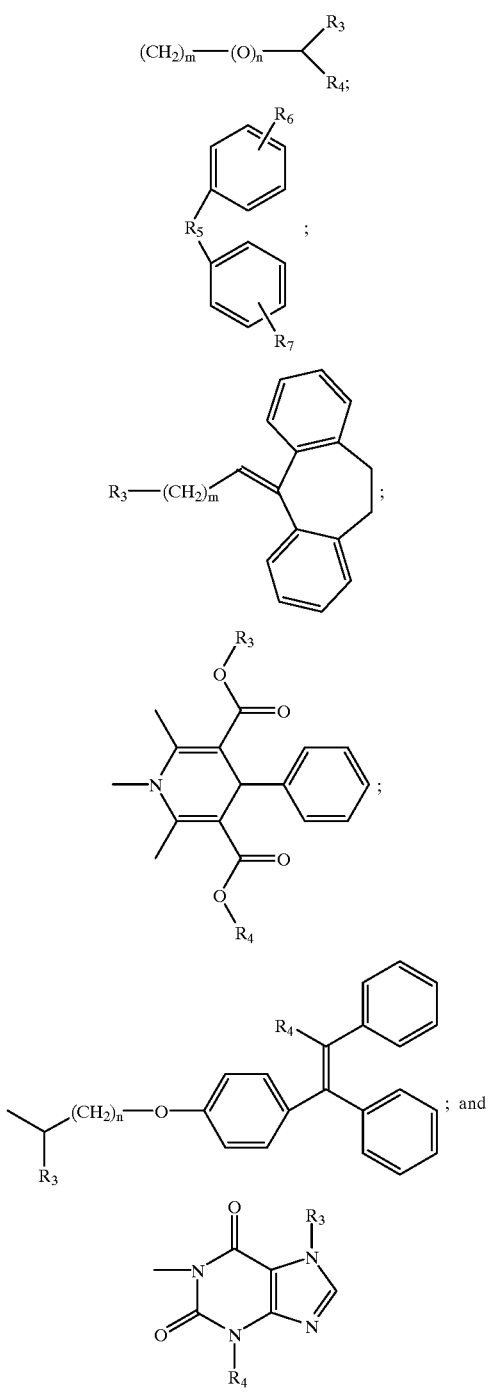

In the general formula (A) above:

R$_1$ and R$_2$ are each one or more independent substituents selected from hydrogen, C1–C5 alkyl, C2–C5 alkenyl, C3–C5 cycloalkyl, C1–C5 alkoxy, C2–C5 alkynyl, halogen, C1–C5 alkoxy, C1–C5 haloalkyl, alkylamino, phenyl, nitro, carboxyl, piperazinyl, pyridyl, and fused ring systems; wherein if R$_1$ or R$_2$ are piperazinyl, a nitrogen atom on each piperazinyl may be substituted with a moiety selected from C1–C5 alkyl, C3–C5 cycloalkyl, C1–C5 haloalkyl, substituted or unsubstituted C1–C5 alkylamino; wherein if R$_1$ or R$_2$ are alkylamino, each alkylamino consists of 1 to 5 carbon atoms and the amino group is unsubstituted or mono- or di-substituted with C3–C5 cycloalkyl, C2–C5 alkenyl, C2–C5 alkynyl or C1–C5 alkyl, and if R$_1$ or R$_2$ is a fused ring system, each individual R$_1$ or R$_2$ involved in the fused ring system, together with the phenyl to which it is attached, forms a fused ring system selected from naphthalene, anthracene, acenaphthylene, fluorene, phenalene, phenanthrene, fluoranthene, acephenanthrylene, aceanthrylene, aceanthrylene, isoindole, indole, quinolizine, isoquinoline, phthalazine, quinoxaline, quinoline, phthalazine, quinazoline, and cinnoline, wherein one or more carbon atoms in the fused ring may be replaced with a nitrogen atom and each ring may be saturated or unsaturated, in whole or in part; wherein each ring may be substituted by one or more substituents selected from halogen, C1–C5 alkyl, C2–C5 alkenyl, C2–C5 alkynyl, and C1–C5 haloalkyl;

R$_3$ is hydrogen, C1–C5 alkyl, C2–C5 alkenyl, C3–C5 cycloalkyl, C2–C5 alkynyl, amino, C1–C5 alkyl-substituted amino, sulfur, oxygen, phenyl, benzyl, naphthyl and anthracenyl; wherein each aromatic ring may be substituted by one or more substituents selected from halogen, C1–C5 alkyl, C2–C5 alkenyl, C2–C5 alkynyl, and C1–C5 haloalkyl;

R$_4$ is hydrogen, C1–C5 alkyl, C2–C5 alkenyl, C3–C5 cycloalkyl, C2–C5 alkynyl, amino, C1–C5 alkyl-substituted amino, C1–C5 alkylamino, C2–C5 alkenylamino, C1–C5 alkyl substituted C1–C5 alkylamino, C1–C5 alkyl substituted C2–C5 alkenylamino, sulfur, oxygen, phenyl, benzyl, naphthyl and anthracenyl; wherein each aromatic ring may be substituted by one or more substituents selected from halogen, C1–C5 alkyl, C2–C5 alkenyl, C2–C5 alkynyl, and C1–C5 haloalkyl;

R$_5$ is nitrogen or carbon;

R$_6$ and R$_7$ are each one or more independent substitutions selected from hydrogen, C1–C5 alkyl, C2–C5 alkenyl, C3–C5 cycloalkyl, C1–C5 alkoxy, C2–C5 alkynyl, halogen, C1–C5 haloalkyl, alkylamino, phenyl, nitro, carboxyl, piperazinyl, pyridyl, and fused ring systems; wherein if R$_6$ or R$_7$ is piperazinyl, a nitrogen atom on each piperazinyl may be substituted with a moiety selected from C1–C5 alkyl, C3–C5 cycloalkyl, C1–C5 haloalkyl, substituted or unsubstituted C1–C5 alkylamino; wherein if R$_6$ or R$_7$ is alkylamino, each alkylamino consists of 1 to 5 carbon atoms and the amino group is unsubstituted or mono- or di-substituted with C3–C5 cycloalkyl, C2–C5 alkenyl, C2–C5 alkynyl or C1–C5 alkyl, and if R$_6$ or R$_7$ is a fused ring system, each individual R$_6$ and R$_7$ involved in the fused ring system, together with the phenyl to which it is attached, forms a fused ring system selected from naphthalene, anthracene, acenaphthylene, fluorene, phenalene, phenanthrene, fluoranthene, acephenanthrylene, aceanthrylene, aceanthrylene, isoindole, indole, quinolizine, isoquinoline, phthalazine, quinoxaline, quinoline, phthalazine, quinazoline, and cinnoline, wherein one or more carbon atoms in the fused ring may be replaced with a nitrogen atom and each ring may be saturated or unsaturated, in whole or in part; wherein each ring may be substituted by one or more substituents selected from halogen, C1–C5 alkyl, C2–C5 alkenyl, C2–C5 alkynyl, and C1–C5 haloalkyl;

n is an integer of from 0 to 5;
m is an integer of from 0 to 5;
or a pharmaceutically acceptable salt of such compound.

Particularly preferred in this regard are compounds of any of formula (I)–(VI) below.

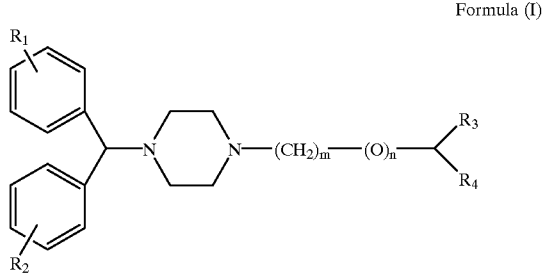

Formula (I)

wherein $R_1$, and $R_2$ can each be one or more independent substituents selected from hydrogen, C1–C5 alkyl, C2–C5 alkenyl, C3–C5 cycloalkyl, C2–C5 alkynyl, nitro and halogen; $R_3$ and $R_4$ can independently be selected from C1–C5 alkyl, C2–C5 alkenyl, C3–C5 cycloalkyl, C2–C5 alkynyl, phenyl, benzyl, naphthyl and anthracenyl. Each aromatic ring may be substituted by one or more substituents selected from halogen, C1–C5 alkyl, C2–C5 alkenyl, C2–C5 alkynyl, and C1–C5 haloalkyl. In Formula (I) m is 0 to 5 inclusive, and n is 0 or 1. Pharmaceutically acceptable salts of these compounds also are encompassed by the present invention.

Particularly preferred compounds in accordance with Formula (I) are those where $R_1$, and $R_2$ are each hydrogen, $R_3$ and $R_4$ are selected from C1–C5 alkyl and benzyl, with each phenyl moiety being unsubstituted or substituted with one or more substituents selected from halogen and haloalkyl, and m and n are each 0. Other compounds of Formula (I) include those where $R_2$ and $R_2$ are each hydrogen, $R_3$ is phenyl, $R_4$ is selected from C1–C5 alkyl and C1–C5 haloalkyl, m is 1 to 5 inclusive and n is 0. Additional compounds include those of Formula (I) where $R_1$ and $R_2$ are each hydrogen, $R_3$ is methyl and $R_4$ is phenyl, wherein $R_4$ is the only substituted phenyl moiety, the substitution selected from halogen and trifluoromethyl. Other preferred compounds include those of Formula (I) where n is 1 or where $R_1$ and $R_2$ are each hydrogen and $R_3$ and $R_4$ are each phenyl.

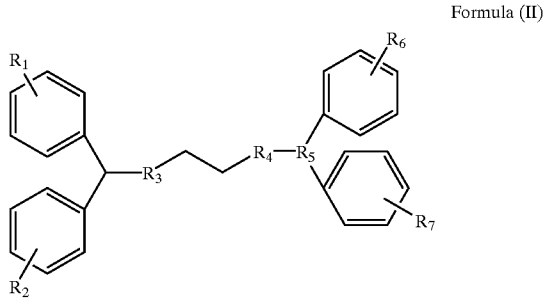

Formula (II)

wherein $R_1$, $R_2$, $R_6$ and $R_7$ can each be one or more independent substituents selected from hydrogen, C1–C5 alkyl, C2–C5 alkenyl, C3–C5 cycloalkyl, C1–C5 alkoxy, C2–C5 alkynyl, halogen, C1–C5 haloalkyl, alkylamino, phenyl, nitro, carboxyl, piperazinyl, pyridyl, and fused ring systems. If any of $R_1$, $R_2$, $R_6$ and $R_7$ are piperazinyl, a nitrogen atom on each piperazinyl may be substituted with a moiety selected from C1–C5 alkyl, C3–C5 cycloalkyl, C1–C5 haloalkyl, substituted or unsubstituted C1–C5 alkylamino. Moreover, if any of $R_1$, $R_2$, $R_6$ and $R_7$ are alkylamino, each alkylamino consists of 1 to 5 carbon atoms and the amino group is unsubstituted or mono- or di-substituted with C3–C5 cycloalkyl, C2–C5 alkenyl, C2–C5 alkynyl or C1–C5 alkyl, and, if any of $R_1$, $R_2$, $R_6$ and $R_7$ is a fused ring system, then each individual R moiety involved in the fused ring system, together with the phenyl to which it is attached, forms a fused ring system selected from naphthalene, anthracene, acenaphthylene, fluorene, phenalene, phenanthrene, fluoranthene, acephenanthrylene, aceanthrylene, aceanthrylene, isoindole, indole, quinolizine, isoquinoline, phthalazine, quinoxaline, quinoline, phthalazine, quinazoline, and cinnoline, wherein one or more carbon atoms in the fused ring may be replaced with a nitrogen atom and each ring may be saturated or unsaturated, in whole or in part. In this case, each ring may be substituted by one or more substituents selected from halogen, C1–C5 alkyl, C2–C5 alkenyl, C2–C5 alkynyl, and C1–C5 haloalkyl. In Formula (II), $R_3$ can be selected from C1–C5 alkyl, C2–C5 alkenyl, C2–C5 alkynyl, amino, C1–C5 alkyl substituted amino, sulfur and oxygen; $R_4$ can be selected from C1–C5 alkyl, C2–C5 alkenyl, C2–C5 alkynyl, amino, C1–C5 alkyl substituted amino, C1–C5 alkylamino, C2–C5 alkenylamino, C1–C5 alkyl substituted C1–C5 alkylamino, C1–C5 alkyl substituted C2–C5 alkenylamino, sulfur and oxygen; and $R_5$, can be nitrogen or carbon. Pharmaceutically acceptable salts of such compounds also are encompassed by the present invention.

Illustrative preferred compounds within Formula (II) are (A) those in which each of $R_1$, $R_2$, $R_6$ and $R_7$ is an independent substituent and also (B) those where, if any of $R_1$, $R_2$, $R_6$ and $R_7$ is a fused ring system, each $R_1$, $R_2$, $R_6$ and $R_7$ moiety involved in the fused ring system, together with the phenyl to which it is attached, forms a fused ring system selected from naphthalene, anthracene, acenaphthylene, fluorene, phenalene, phenanthrene, fluoranthene, acephenanthrylene, aceanthrylene, aceanthrylene, isoindole, indole, quinolizine, isoquinoline, phthalazine, quinoxaline, quinoline, phthalazine, quinazoline, and cinnoline. With respect to category (A), $R_1$, $R_2$, $R_6$ and $R_7$ preferably are selected from hydrogen, C1–C5 alkyl, C2–C5 alkenyl, C3–C5 cycloalkyl, C1–C5 alkoxy, halogen, C1–C5 haloalkyl, alkylamino, phenyl, nitro, piperazinyl, and pyridylmi; if any of $R_1$, $R_2$, $R_6$ and $R_7$ are piperazinyl, a nitrogen atom on each piperazinyl may be substituted with a moiety selected from C1–C5 alkyl, C3–C5 cycloalkyl, C1–C5 haloalkyl, substituted or unsubstituted C1–C5 alkylamino, and if any of $R_1$, $R_2$, $R_6$ and $R_7$ are alkylamino, each alkylamino can consist of 1 to 5 carbon atoms and the amino group can be unsubstituted or mono-substituted or di-substituted with C3–C5 cycloalkyl, C2–C5 alkenyl, C2–C5 alkynyl or C1–C5 alkyl. Even more preferred in this regard are compounds of Formula (II) where $R_1$, $R_2$, $R_6$ and $R_7$ are each selected from hydrogen and C1–C5 alkyl, and $R_5$ is carbon. A more preferred compound is where $R_1$, $R_2$, $R_6$ and $R_7$ are each hydrogen, $R_3$ is C1–C5 alkyl and $R_4$ is selected from C1–C5 alkyl and oxygen.

Other preferred compounds useful in the present invention include those where $R_1$, $R_2$, $R_6$ and $R_7$ are each hydrogen, $R_3$ is selected from amino and C1–C5 alkyl substituted amino and $R_4$ is selected from oxygen, sulfur, or C1–C5 alkyl, or where $R_1$, $R_2$, $R_6$ and $R_7$ are each hydrogen, $R_3$ is sulfur and $R_4$ is selected from oxygen, sulfur or C1–C5 alkyl, or where $R_1$, $R_2$, $R_6$ and $R_7$ are each hydrogen, $R_3$ is oxygen and $R_4$ is C1–C5 alkenyl. In addition to those compounds mentioned above, other preferred compounds useful in this invention include those of Formula (II) where $R_1$ and $R_6$ are each hydrogen, $R_2$ and $R_7$ are each methyl, $R_3$ is selected from amino and C1–C5 alkyl substituted amino, and $R_4$ is C1–C5 alkenyl, or where $R_1$ and $R_6$ are each methyl, $R_2$ and $R_7$ are each hydrogen, $R_3$ is oxygen and $R_4$ is C2–C5 alkenylamino. Other preferred compounds are those where $R_5$ is nitrogen, and where $R_1$, $R_2$, $R_6$ and $R_7$ are each hydrogen, $R_3$ is selected from oxygen, nitrogen and C1–C5 alkyl and $R_4$ is C1–C5 alkyl.

Other preferred compounds useful in the present invention include those where $R_3$ and $R_4$ are each oxygen and $R_5$ is carbon, and $R_1$, $R_2$, $R_6$ and $R_7$ are each a single substitution selected from hydrogen, halogen, C1–C5 haloalkyl, C1–C5 alkyl, C1–C5 alkoxy, substituted or unsubstituted piperazinyl, alkylamino, phenyl, and fused ring systems, and preferably $R_1$, $R_2$, $R_6$ and $R_7$ are selected from hydrogen, chlorine, methoxy, trifluoromethyl, methylamino, piperazinyl, phenyl and fused ring systems, and wherein if any of $R_1$, $R_2$, $R_6$ and $R_7$ is a fused ring system, each individual $R_1$, $R_2$, $R_6$ and $R_7$ involved in the fused ring system, together with the phenyl to which it is attached, forms a fused ring system selected from naphthalene, anthracene, acenaphthylene, fluorene, phenalene, phenanthrene, fluoranthene, acephenanthrylene, aceanthrylene, aceanthrylene, isoindole, indole, quinolizine, isoquinoline, phthalazine, quinoxaline, quinoline, phthalazine, quinazoline, and cinnoline, wherein each ring may be substituted by one or more substituents selected from halogen, C1–C5 alkyl, C2–C5 alkenyl, C2–C5 alkynyl, and C1–C5 haloalkyl.

Even more preferred in this regard are compounds of Formula (II) where $R_1$, $R_2$, $R_6$ and $R_7$ are selected from hydrogen, chlorine, C1–C5 alkoxy, trifluoromethyl, substituted or unsubstituted methylamino, piperazinyl, and phenyl, preferably selected from hydrogen, chlorine, and trifluoromethyl and more preferably are hydrogen. Moreover, $R_1$ and $R_6$ may be hydrogen and $R_2$ and $R_7$ may be chlorine, or vice versa, or where $R_1$ and $R_6$ can be any one of trifluoromethyl, C1–C5 alkyl, methyl or a part of a fused ring, and $R_2$ and $R_7$ are hydrogen, or vice versa. Other compounds useful in the present invention are those where $R_1$, $R_2$, $R_6$ and $R_7$ are each alkylamino, wherein each alkylamino consists of 1 to 5 carbon atoms and the amino group is unsubstituted or mono- or di-substituted C1–C5 alkyl, C2–C5 alkenyl, or C2–C5 alkynyl.

Additional useful compounds of the present invention are those of formula (II) where $R_1$ and $R_6$ are each alkylamino, wherein each alkylamino consists of 1 to 5 carbon atoms and the amino group is unsubstituted or mono- or di-substituted C1–C5 alkyl, C2–C5 alkenyl, or C2–C5 alkynyl, and $R_2$ and $R_7$ are hydrogen, or where each of $R_1$, $R_2$, $R_6$ and $R_7$ is selected from hydrogen, phenyl and fused ring systems, wherein if any of $R_1$, $R_2$, $R_6$ and $R_7$ is a fused ring system, each individual R group involved in the fused ring system, together with the phenyl to which it is attached, forms a fused ring system selected from naphthalene, anthracene, acenaphthylene, fluorene, phenalene, phenanthrene, fluoranthene, acephenanthrylene, aceanthrylene, aceanthrylene, isoindole, indole, quinolizine, isoquinoline, phthalazine, quinoxaline, quinoline, phthalazine, quinazoline, and cinnoline, wherein one or more carbon atoms in the fused ring may be replaced with a nitrogen atom and each ring may be saturated or unsaturated, in whole or in part, or more preferably, if any of $R_1$, $R_2$, $R_6$ and $R_7$ is a fused ring system, each individual R group involved in the fused ring system, together with the phenyl to which it is attached, forms a fused ring system selected from naphthalene, anthracene, acenaphthylene, fluorene, phenalene, phenanthrene, fluoranthene, acephenanthrylene, aceanthrylene, aceanthrylene, isoindole, indole, quinolizine, isoquinoline, phthalazine, quinoxaline, quinoline, phthalazine, quinazoline, and cinnoline, or even more preferably $R_1$ and $R_6$ are piperazinyl or alkoxy and $R_2$ and $R_7$ are hydrogen.

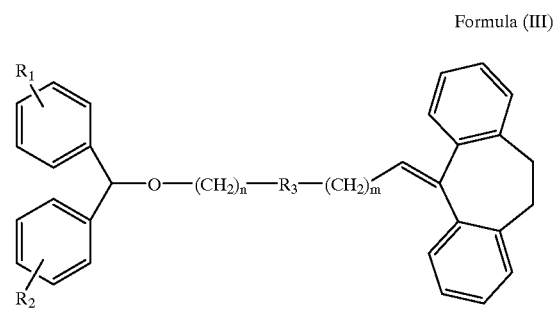

Formula (III)

wherein $R_1$ and $R_3$ can each be one or more independent substituents selected from hydrogen, C1–C5 alkyl, C2–C5 alkenyl, C3–C5 cycloalkyl, C1–C5 alkoxy, C2–C5 alkynyl, halogen, C1–C5 haloalkyl, alkylamino, phenyl, nitro and carboxyl. In Formula (III), $R_3$ can be selected from amino, C1–C5 substituted amino and $CH_2$; and n and m can independently be and integer of from 0–5. Pharmaceutically acceptable salts of these compounds also are encompassed by the present invention.

Particularly preferred compounds of Formula (III) include those where $R_1$, and $R_2$ are each hydrogen, $R_3$ is methylamino, and n and m are each 2, and more preferably where $R_1$ and $R_2$ are each hydrogen and $R_3$ is $CH_2$.

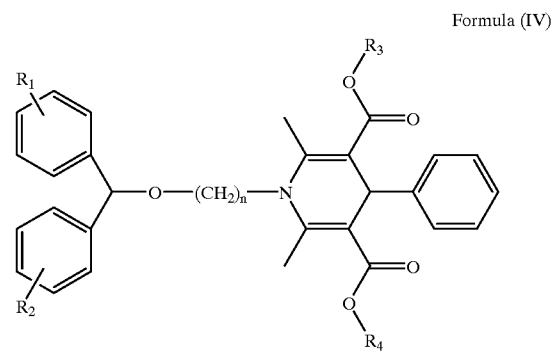

Formula (IV)

wherein $R_1$ and $R_2$ each can be one or more independent substituents selected from hydrogen, C1–C5 alkyl, C2–C5 alkenyl, C3–C5 cycloalkyl, C1–C5 alkoxy, C2–C5 alkynyl, halogen, C1–C5 haloalkyl, alkylamino, phenyl, nitro and carboxyl. $R_3$ and $R_4$ each can be independent and selected from hydrogen and C1–C5 alkyl, and n can be 1 to 5 inclusive. Pharmaceutically acceptable salts of these compounds also are encompassed by the present invention.

Particularly preferred compounds of Formula (IV) include those where $R_1$ and $R_2$ are each hydrogen, $R_3$ and $R_4$ are each methyl, and n is 2.

Formula (V)

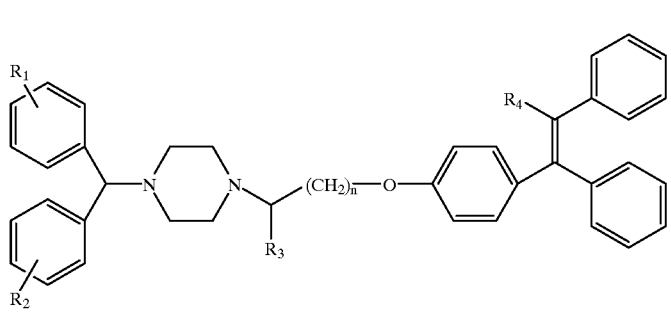

wherein $R_1$ and $R_2$ each can be one or more independent substituents selected from hydrogen, C1–C5 alkyl, C2–C5 alkenyl, C3–C5 cycloalkyl, C1–C5 alkoxy, C2–C5 alkynyl, halogen, C1–C5 haloalkyl, alkylamino, phenyl, nitro and carboxyl. $R_3$ can be selected from hydrogen and C1–C5 alkyl, $R_4$ can be selected from hydrogen and C1–C5 alkyl, and n can be 1 to 5 inclusive. Pharmaceutically acceptable salts of these compounds also are encompassed by the present invention.

Particularly preferred compounds of formula (V) are those where $R_1$ and $R_2$ are each hydrogen, or where $R_3$ is methyl, and n is 1.

Formula (VI)

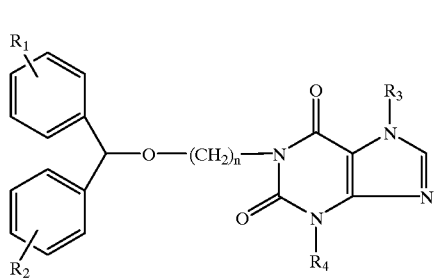

wherein $R_1$ and $R_2$ each can be one or more independent substituents selected from hydrogen, C1–C5 alkyl, C2–C5 alkenyl, C3–C5 cycloalkyl, C1–C5 alkoxy, C2–C5 alkynyl, halogen, C1–C5 haloalkyl, alkylamino, phenyl, nitro and carboxyl. $R_3$ and $R_4$ each can be independent and selected from hydrogen and C1–C5 alkyl, and n is 1 to 5 inclusive. Pharmaceutically acceptable salts of these compounds also are encompassed by the present invention.

Particularly preferred compounds of Formula (VI) include those where $R_1$ and $R_2$ are hydrogen, where $R_3$ is hydrogen, $R_4$ is methyl and n is 2, or where $R_3$ is methyl, $R_4$ is methyl and n is 2.

Any of these compounds can be formulated into a pharmaceutically acceptable composition for administration to a mammal or test animal whereby the composition would include a pharmaceutically acceptable carrier and a therapeutically effective amount of the compound.

Skilled artisans are capable of synthesizing any of the aforementioned compounds using methods known to those skilled in the art. The following synthesis pathways illustrate how various compounds can be made in accordance with the present invention.

Synthesis Pathway for Compounds of Formula (I):

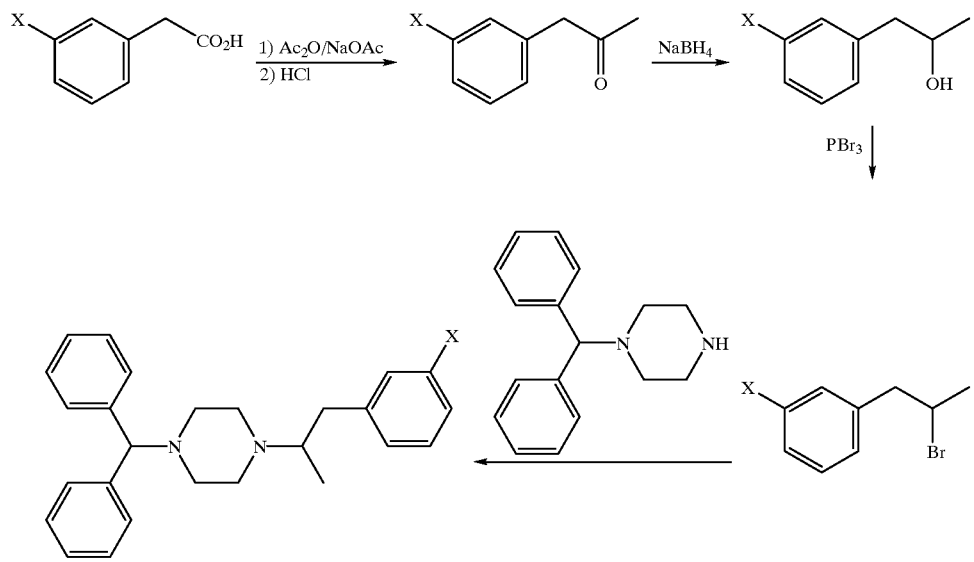

where x can be selected from H, Cl, CF$_3$ or C1–C5 alkyl.
Synthesis Pathway for Compounds of Formula (II):
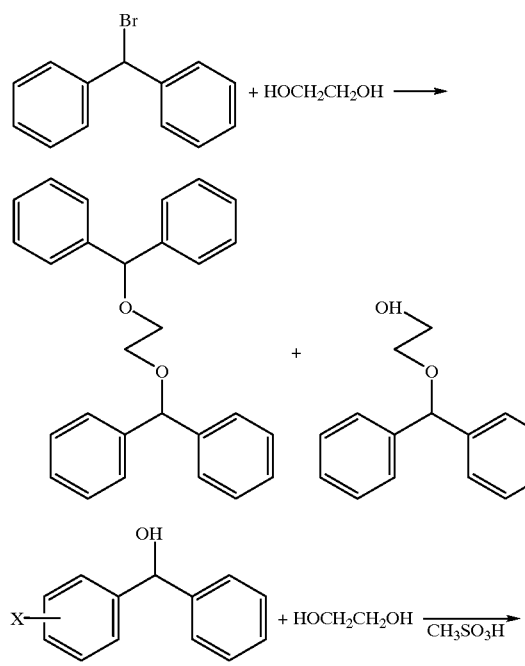
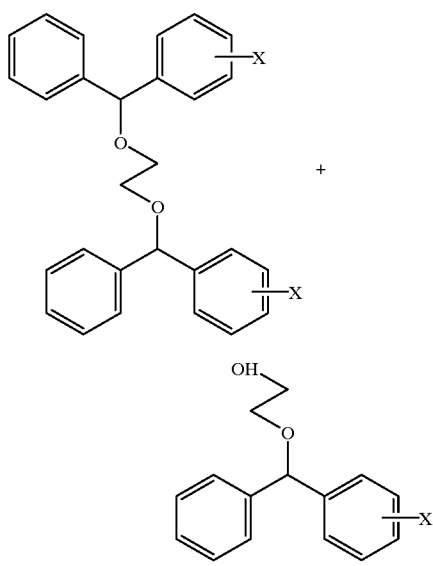
where x can be CH$_3$, OCH$_3$, CF$_3$, Cl, Br, F or other halogen, CO$_2$R, NR$_3$, cyclohexane, naphthyl, SO$_3$ or CONH$_2$, where R can be hyrogen or C1–C5 alkyl.
Synthesis Pathway for Compounds of Formula (III):
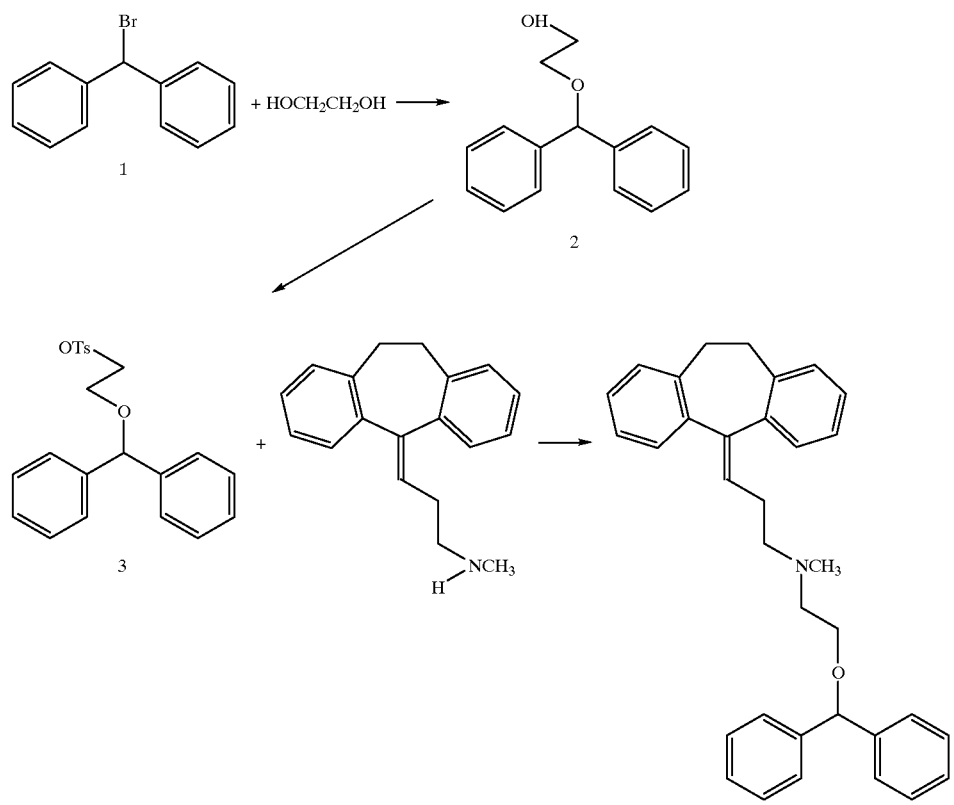

where Ts denotes a tosylate derivative.

Synthesis Pathway for Compounds of Formula (IV):

Compounds of Formula (IV) can be prepared using techniques known in the art. For example, compound 3 from the Formula (II) compound synthesis can be modified by replacing the OH with NH₂, and then this compound can be used in the Hantzsch pyridine synthesis, together with benzylaldehyde and a β-keto ester. the Hantzsch pyridine synthesis is described, for example, in Streitwieser, INTRODUCTION TO ORGANIC CHEMISTRY, Macmillan Publishing Co., Inc., N.Y. 1097 (1976). An exemplary synthesis pathway is illustrated below.

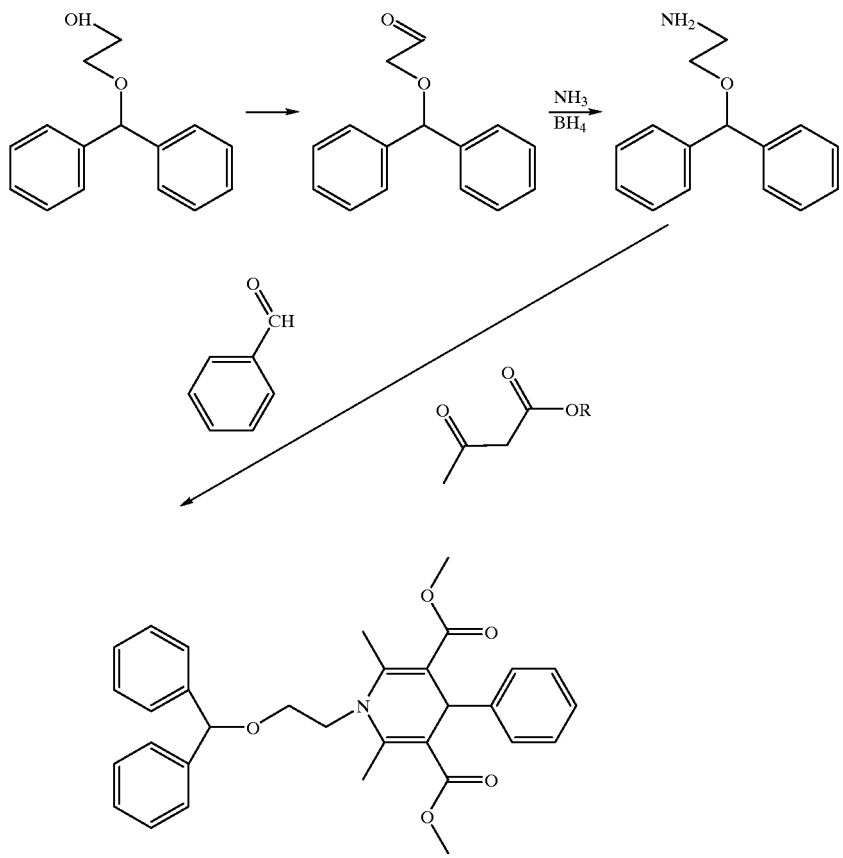

where R can be any unsubstituted or substituted alkyl radical having from 1–5 carbon atoms.

Synthesis Pathway for Compounds of Formula (V):

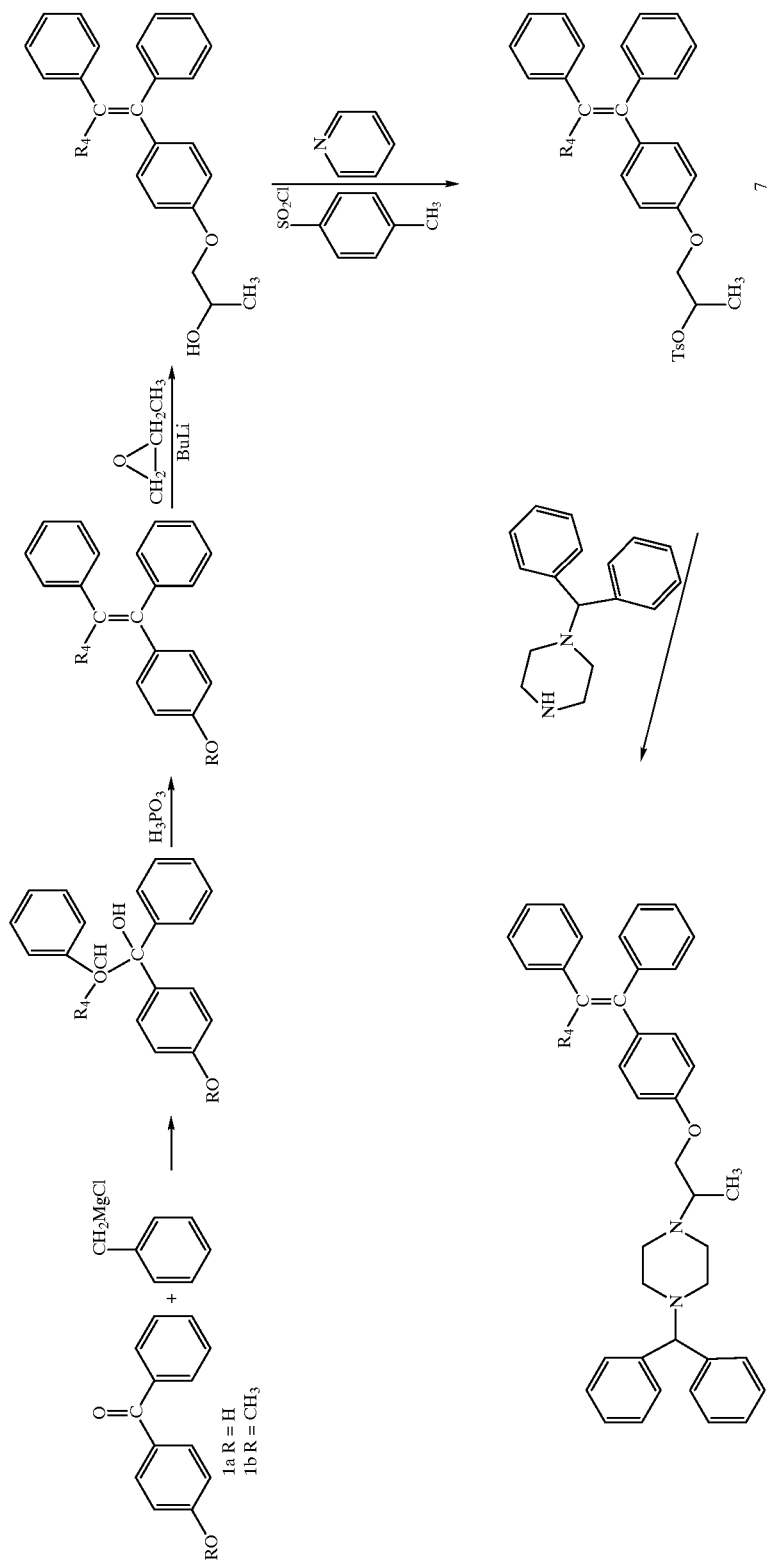

where $R_4$ can be H or C1–C5 alkyl, and where Ts denotes tosylate. If R is $CH_3$, the methyl group can be removed by conventional means, including, for example, reaction with NaCN.

Synthesis Pathway for Compounds of Formula (VI):

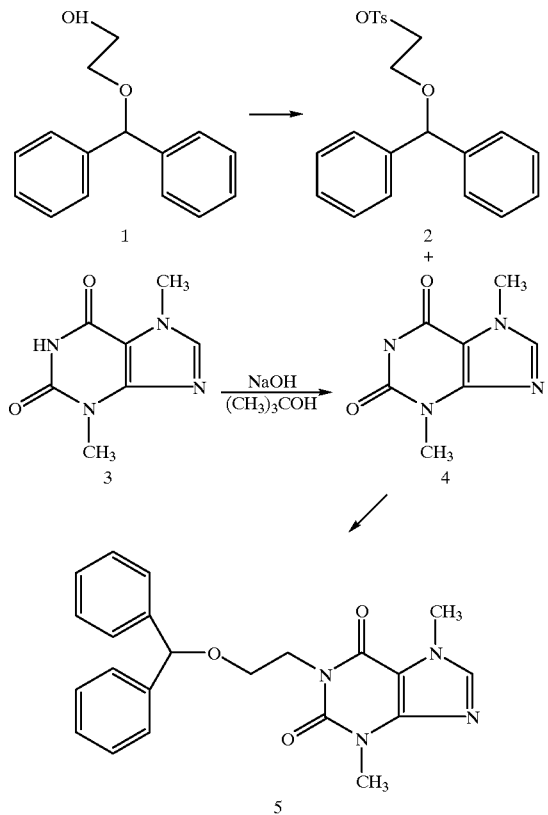

where Ts represents a tosylate derivative, and compound number 2 is the same as compound number 3 in the synthesis of Formula (III) compounds. Those skilled in the art will appreciate that other routes can be used to synthesize any of the compounds of Formula (I)–(VI), using the guidelines provided herein.

The microspheric bodies (DMS) employed according to the present invention are derived from mammalian brain tissue and are characterized, in essentially homogeneous form, by a range of diameters from about 0.1 μm to about 15 μm, by the proteinaceous core structure of DMS, and by certain stainability properties. (In this regard, "homogeneous" means that the DMS represent the only protein structure discernible in the subject composition at the light-microscopic level.) For example, the microscopic bodies of the present invention are homogeneously electron-dense when stained with osmium and lead, and can be visualized by thin-section electron microscopy; under optical microscopic examination, they appear eosinophilic and phloxinophilic, and are nonbirefringent when stained with Congo Red. When the microspheric bodies of the present invention are disrupted, a material is produced that displays congophilic birefringence; that is, when stained with Congo Red the material becomes optically anisotropic to the extent of splitting an incident light wave into two waves with mutually perpendicular vibrational planes and produces a red-green color change when viewed with cross polarizers.

DMS are spherical, membrane-bounded, intracellular structures, about 0.1 and 15 μm in diameter, that are found in human and other mammalian brains. More specifically, the normal location for DMS is in gray-matter neuropil, where the spherical structures are enclosed in tiny, neuronal cellular processes. DMS are solitary, non-perikaryal and non-confluent, and are not found in cerebellum or in white matter. With regard to inter-DMS distances, the spatial distribution of DMS in gray matter regions is random. Compositions of DMS in homogeneous form can be produced by extraction, according to the present invention, to give homogeneous samples of DMS.

The following procedure can be followed to extract DMS from brain tissue:

(1) Whole brain is removed from the skull postmortem, by use of standard postmortem techniques for humans or animals. The best results are obtained if the organism has been in circulatory arrest for less than six hours at the time of brain removal and if the body has been refrigerated as early as possible postmortem. DMS are still extractable at postmortem intervals greater than six hours and are still extractable if body cooling has been delayed or absent, but these two factors will usually greatly decrease the overall average yield of DMS per individual brain. In addition to the effect of postcirculatory arrest interval and temperature on DMS yield, there is considerable individual variation in DMS content per brain, and also individual variation in DMS extractability, which may be related to agonal metabolic state, overall disease status or other factors. All of the factors which determine total DMS yield per brain can have an impact on DMS extraction, since the volume of homogeneous DMS will decrease proportionally to any reduction in percentage extractability; such a decrease may be sufficient to hinder accurate recognition during the extraction procedure. Furthermore, the screening of putative anti-amyloidosis therapies and the characterization of isolated samples of DMS, in accordance with the present invention, are rendered correspondingly more difficult and costly, and ultimately may be impossible at critically small volumes of DMS.

(2) By means of clean instruments, the freshly removed brain is immediately dissected. Dissection is optimally performed in a cold room at 10° C. By means of careful, but rapid, sharp and blunt dissection, the internal capsules, corona radiata, centra semi-ovale, brain stem, cerebellum, lepto and pachymeninges, arachnoid granulations, coroid plexi, and blood vessels are separated and discarded, and the remaining mass of brain is rapidly used for the subsequent steps. (Standard blocks for microscopic study can be removed at this stage and stored separately in histological fixative.) The dissection brain mass ("DBM") is optimally utilized immediately after dissection. It may also be stored frozen at temperatures of –10° C. to –70° C., but this decreases the overall average yield of DMS per individual brain.

(3) The extraction of DMS material from DBM can be carried out by a combination of centrifugation steps. In an exemplary extraction, DBM mechanically homogenized in a 2:1 volume of 0.5 M TRIS-HCL buffer (pH 7.5) is subjected to centrifugation at about 200 rpm for some 10 minutes. (All manipulations are carried out at around 4° C.) The sediment thus obtained ("Sediment I") is separated across a sucrose gradient (1.589 M, or 45%; 1.895 M, or 52%; 2.3895 M, or 62.5%) via centrifugation at 26,000 rpm for 30 minutes. It has been found that the material that settles at the interface between 1.895 M and 2.1015 M (56.7% sucrose) is the DMS containing fraction, as may be confirmed by microscopic examination, with eosin staining, of the fraction.

The DMS-containing fraction obtained from Sediment I consists essentially of the dense microspheres described above, and can be used in a screening method according to the present invention. It is preferable, however, for the fraction to be subjected to additional manipulations in order to enrich the DMS concentration. To this end, it has proved useful, for example, to wash the DMS-containing fraction in buffer—the above-mentioned homogenization buffer is suitable for this purpose—and to spin the resulting mixture again (10,000 rpm for 7 minutes) to obtain DMS-enriched sediment ("Sediment II").

As with Sediment I, Sediment II can be run through a density gradient to enrich further the yield of DMS. It has been discovered that the carbohydrate Percoll® (Pharmicia) is particularly useful in this context. A commercially available formulation of 80% Percoll® (1.13 g/ml) in 0.15 M NaCl provides a iso-osmolar gradient to which Sediment II can be subjected (30,000 rpm for 15 minutes); successive samples, on the order of 0.25 to 1 cc each, then can be taken along the length of the gradient and the DMS-enriched fractions isolated. If these fractions are washed again in buffer, they can be spun down once again (15,000 rpm for 10 minutes) to obtain a sediment ("Sediment III") that is substantially pure DMS.

The DMS materials obtained as described above can be used, pursuant to the present invention, in screening anti-amyloidosis therapies. In particular, homogeneous DMS material within the present invention can be employed to ascertain effectiveness in vitro, on the part of an active agent or a treatment comprising a putative therapy for cerebral amyloidosis, in reducing the extent of DMS disruption induced by autocatalytic DMS disruption.

By whatever means DMS are disrupted in control samples, a putative anti-amyloidosis agent or therapy can be screened by virtue of its ability to reduce the volume of tissue occupied by the redistributed transformed DMS protein material and associated injury foci under test conditions. For example, in vitro DMS disruption on an appropriate viewing surface, such as a glass or plastic slide (see Test 1 below), can be accomplished by mechanical means; by the action of an enzyme treatment, or other chemical exposure. Disruption of DMS can also be effected by injecting DMS material of the present invention into an isolated tissue sample (see Test 2). Brain slices are preferred for this purpose, but liver, pancreas and other organs are also acceptable sources for tissue samples.

An active agent or a treatment that proves effective in vitro is then tested, pursuant to the present invention, for in vivo efficacy in preventing amyloid-fibril formation by reducing the number, quantity and volume of DMS disruption (to thereby reduce and/or prevent future DMS disruption) in an animal model for cerebral amyloidosis comprised, for example, of a rat, dog, cat or other suitable laboratory animal that has been injected with homogeneous DMS material, pursuant to the present invention. Although intracerebral injection is preferred, injection sites in a test animal's body other than in the brain, such as in skin and in muscle, are suitable for determining the ability of a proposed active agent or treatment step to hinder the resulting formation of amyloid. Because simple injection of DMS onto a glass slide does not result in amyloid formation, it is understood that in vivo production of amyloid fibrils upon injection of DMS occurs in the extracellular spaces of the injected tissue.

For the present invention, an active agent is useful, when present at in tissue concentrations of $10^{-5}$ M or less (e.g., between $10^{-5}$ M and $10^{-6}$ M) in DMS-injected test animals, if it prevents DMS disruption or, in relation to an untreated or placebo control, if it: (i) reduces the mean volume of tissue occupied by the redistributed, transformed DMS protein material; (ii) reduces the ratio of the number of inflammatory cells per DMS; or (iii) increases the ratio of the number of macrophages containing disrupted DMS material per DMS.

As a further refinement, substances falling within this newly-defined category of pharmaceutically active agents—that is, the class of compounds that, at $\leq 10^{-5}$ M concentration levels in tissues, inhibit DMS disruption and/or transformation and hence, inhibit induced amyloid formation—can be tested, pursuant to the present invention, in a second in vivo assay. Particularly preferred for this purpose is the "senile animal" model for cerebral amyloidosis, where animals such as aged dogs or monkeys, which are known to develop variable numbers of Alzheimer-type cerebral senile plaques, see Wisniewski, et al., *J. Neuropathol. & Exp. Neurol.* 32: 566 (1973); Selkoe, et al., *Science* 235:873 (1987), are tested for amyloid inhibition. This in vivo assay involves initial pretreatment- and control-biopsy monitoring, to confirm and quantify the presence of senile plaque, and serial cerebral biopsy to monitor quantitatively the evolution of DMS and senile plaque in situ and the presence (or absence) of amyloid-formation inhibition.

The method of the present invention for treating cerebral amyloidosis is used with subjects in whom amyloid formation is anticipated. The treatment can be applied, for example, to those who are at risk of developing cerebral amyloid, as in senile plaques, including the elderly, nondemented population and patients with the diagnoses listed above under the cerebral-amyloidosis rubric. In addition, such prophylactic therapy can be effected, pursuant to the present invention, to inhibit or prevent less severe forms of brain-function decline correlated with the formation of smaller amounts of disrupted DMS in elderly, nondemented subjects for whom there is not expectation of dementia associated with a diseases under the cerebral-amyloidosis rubric.

Compounds within the present invention can be administered to such subjects orally, rectally, via a nasal route, parenterally (including by skin or other routes), in spray or aerosol form, or via inhalation. A compound within the present invention can thus be administered in a pharmaceutically-acceptable carrier therefor, such as physiological saline solution.

Compounds of the present invention are particularly preferred that, in addition to possessing DMS disruption inhibiting activity in the aforementioned concentration range, also are nontoxic at an appropriate dosage level, have a satisfactory duration of effect, and display an adequate ability to cross the blood-brain barrier. In this regard, U.S. Pat. No. 4,540,564 discloses an approach for enhancing blood-brain barrier-penetrating ability by attaching a centrally acting drug species to a reduced, biooxidizable, lipoidal form of a dihydropyridine≈pyridinium salt redox carrier. Also particularly preferred are compounds that have specific, selective binding affinity for DMS components. Skilled artisans recognize that any of the known methods of enhancing blood-brain barrier-penetrating ability can be used in the present invention, using the guidelines provided herein.

Determining a pharmaceutically-effective amount of a compound administered in accordance with the present invention entails standard evaluations of pharmacokinetic data and clinical efficacy. For instance, see GOODMAN AND GILMAN'S THE PHARMACOLOGICAL BASIS FOR THERAPEUTICS (7th ed.). Thus, the above-described in vivo animal testing will provide the basis for a range of dosages and dosage schedules to be assessed clinically in humans. An assessment in this regard would generate pharmacokinetic data, for example, regarding bioavailability, absorption, metabolism, serum levels and excretion.

Such data would be evaluated against clinical data obtained concurrently from neurobehavioral testing, for example, memory testing and testing of cognitive function, and from clinical medical assessment. If a dosage halts progression of deterioration in clinical parameters for a symptomatic patient, i.e., a subject diagnosed as suffering from cerebral amyloidosis, that dosage should also have a prophylactic effect in the elderly, nondemented population. In addition, a pharmaceutical composition within the present invention could be employed to ameliorate or prevent a decline in brain function, associated with amyloid formation, that is less severe than dementia, for example, where the subject does not require supervision or nursing care.

Prophylactic therapy in the aforementioned population could be effected, pursuant to the present invention, for all persons of normal brain function who fall within a prescribed age group, for example, 65- or 70-to-75-years old. Alternatively, prophylactic therapy could be applied to nondemented persons of any age who, while displaying normal brain function, are identified via diagnostic testing that reveals evidence of DMS disruption in the brain.

Diagnostic testing of this sort can be conducted by assaying, immunologically or otherwise, for the presence of DMS components such as DMS membrane, DMS protein or fragments thereof in biological samples other than brain tissue, such as samples of serum, spinal fluid and other bodily fluids. Testing can also be directed to detection in a subject of antibodies against one or more DMS components. In addition, prophylactic therapy according to the present invention can be administered to the nondemented population on the basis of other factors, suggesting a risk for dementia, which are revealed by radiological or diagnostic imaging, genetic testing, electroencephalography or other means.

The following test paradigms illustrate ways in which DMS material, as described above, can be employed routinely, according to the present invention, in identifying anti-amyloidosis agents within the aforementioned class of compounds.

TEST 1: In vitro disruption of DMS in a human brain slice

Human brain postmortem samples of histological block size (usually 1–5 cm×1–5 cm×1–3 mm) are removed, by sterile techniques, with the aid of sterile gloves, scalpel and forceps, and then are placed in sterile empty plastic containers, such as a Petri dish before extracted DMS are injected into each brain sample at room temperature. After a one-hour incubation at room temperature, the brain samples are immersed in histological fixative and processed from histology by techniques that are standard for optical microscopy. Controls, size of inoculum, preparations of slides and interpretation of results are described below.

TEST 2: Formation of disrupted DMS induced in vivo by injection of DMS into live tissue Laboratory rodents are anesthetized and their brains immobilized by routine methods, and injections of homogeneous DMS are made into superficial cerebral cortex regions through sterile needles inserted through the skull and meninges. (Sham control injections of DMS negative material can be put into either the contralateral cortex or into separate animals.) The method of anesthesia, type of craniotomy, site of injections in the brain parenchyma, size of needle and syringe or other vehicle, would closure technique, and numbers of animals used are not crucial to the test and will vary depending on the animal used. Thus, a small mouse may not need a skull flap whereas a larger mammal may need a burr hole; size of needles or vehicles may vary with animal brain size, etc. (see Example 1). The size of injection is elective; smaller injections are more difficult and costly to trace histologically (see below), but larger injections are more costly in terms of numbers of DMS used. An exemplary protocol is detailed in Example 1.

The animal is painlessly sacrificed about 30 minutes or more after injection. The exact time of sacrifice is elective; generally, a period of 1 to 24 hours is preferable, but the DMS transformation will persist and can be recognized at many time intervals. After sacrifice the brain is removed by standard methods and immersion fixed in histological fixative. Perfusion fixation is not recommended because perfusion pressures will usually disrupt the injection cavity and render the results inaccessible.

According to standard methods, the brain is fixed in toto for several days (correspondingly longer for larger animal brains), sliced, embedded, cut, mounted and stained for histological study. A dissecting microscope is used to locate the injection site and accurately place it in the block, and sections are carefully inspected during microtomy to ensure that the injection site is in the section and not discarded during trimming. The mounted slides are stained with routine stains such as hematoxylin-eosin, or Congo Red, according to standard methodology. The sections are examined with the optical microscope fitted with polarizing lenses.

Variations are possible by virtue of the fact that compounds can be administered in vivo, via injection, ingestion or other routes, before, after or during the introduction of DMS, and concurrently with or separately from the DMS. In addition, therapeutic strategies other than those based on the action of a pharmacological agent can be studied in whole animals. By means of the foregoing tests, nontoxic compounds suitable for clinical testing in human beings can be identified, pursuant to the present invention, that reduce the number, quantity and/or volume of disrupted DMS.

Other details of the present invention are further described by reference to the following illustrative examples.

EXAMPLE ONE

Two human brain postmortem samples of 1.5 cm.×1.5 cm.×2 mm were removed by sterile technique and placed in two sterile Petri dishes. Approximately 80,000 homogeneous extracted DMS were injected into each through a sterile 20 gauge stainless steel needle at 37° C. Acetylcholine 20 mm in physiological saline was added to the second injection as a possible test compound. After one hour's incubation both samples were immersed and processed as in Test 1 above.

EXAMPLE TWO

This example illustrates the identification of compounds, via an in vivo assay, as effective in reducing the number, quantity and/or volume of disrupted DMS, and hence, a effective amyloid-formation inhibitors at physiologically-compatible concentrations.

IN VIVO ASSAY: Male Wistar rats of three-months age are anesthetized by ether inhalation. Their heads are immobilized by means of a stereo-tactic head brace. Bilateral parieto-occipital scalp incisions (1 cm) are made with a sterile scalpel blade. Bilateral parieto-occipital 0.5 mm burr holes are made with a 0.5 mm drill.

For each compound to be assayed (see below), six rats are each injected on one side, through the burr hole from a sterile 1 cc syringe fitted with a sterile 22 gauge needle, with sterile physiological saline containing about 400,000 human DMS and the compound (total volume: 100 μl). The injection is made in to the cerebral cortex to a depth of a few millimeters, so that the injection is within the parenchyma, not on the surface or in the ventricles. Consequently, the in-tissue concentration of the compound at the site of injection corresponds to the concentration of the compound in the saline.

On the contralateral side, each of the six test rats also receive an injection of sterile physiological saline (100 μl). In addition to this internal control, a control group of six rats that do not receive any injection is associated with each test group. As an additional control group, a group of six rats that receive an injection of DMS without the compound, or that receive an injection of DMS and a compound found inactive using the testing protocols described herein, is associated with each test group.

After injection of the test animals, a sterile suture is placed through the scalp incision to cover the wound, and the animals are observed. Injection can be intracerebral, or via in-tissue injection at other places on the test animal. At post-injection intervals of one hour, twelve hours and twenty-four hours, respectively, four animals (two from the test group and two controls) are painlessly sacrificed by ether inhalation and $CO_2$ insufflation. Their brains are removed and fixed via immersion for twenty-four hours in 10% formalin. The fixed tissue is then sliced coronally, in sections of between 0.5 mm and 1 mm in thickness, and the areas of injection are dissected out and blocked as described above under "Test 2."

The blocks with the injection site are sectioned at a thickness of 6 μm, and every tenth section is mounted to provide a total of ten technically intact sections containing the injection site. The mounted sections are processed and stained with Congo Red, as previously described, and examined, via optical microscopy, with and without polarized illumination. By means of optical micrometer and standard graticles, mean volumes of DMS is determined and compared to the controls. Compounds that were found to reduce the number, quantity and/or volume of disrupted DMS, when compared to the controls, were selected according to the present invention. Those compounds that did not reduce the number, quantity and/or volume of disrupted DMS, or that did not significantly reduce the number, quantity and/or volume of disrupted DMS, when compared to the controls, were considered inactive. Some of these inactive compounds were used in subsequent experiments as controls.

EXAMPLE 3

Approximately 500 compounds were tested as described in example 2 above. Those compounds that were found to reduce the number, quantity and/or volume of disrupted DMS by at least 10%, when compared to the controls, were considered useful in the present invention. The compounds found to be useful were found to fall within six (6) general formula, described below in Examples 4 and 5, whereas those compounds that did not reduce the number, quantity and/or volume of disrupted DMS by at least 10%, when compared to the controls, did not fall within the six (6) general formula.

EXAMPLE 4

This example illustrates the synthesis of various compounds used in Examples 1 and 2 above, which were found to be effective.

1. Synthesis of compounds of formula (I)

Preparation of (±)-1-(1-Phenylisopropyl)-4-(diphenylmethyl)piperazine

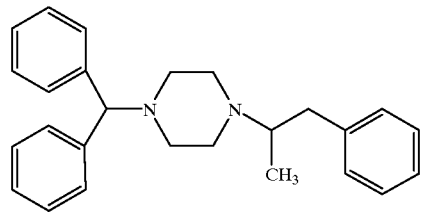

Compound 1

The general pathway for making compounds of Formula (I) is outlined above. In accordance with the general pathway, approximately 17 g of 0.1 mol 3-Chlorophenylacetic acid was refluxed in acetic anhydride (75 ml, 0.8 mol) and sodium acetate (8.2 g., 0.1 mol) for 2 days. The resulting mixture was allowed to cool to room temperature and diluted with water (150 ml). The organic layer was then refluxed in concentrated HCl (80 ml) for one hour, cooled to room temperature and then 200 ml of water was added to the mixture. The mixture was extracted with ethyl ether to produce 2-chlorophenyl acetone at about a 41% yield. The intermediate product had a boiling point of about 76° C.

To a solution of 3-chlorophenyl acetone (8.1 g, 48 mmol) in ethanol (50 ml) was added $NaBH_4$ (1.5 g, 40 mmoles). The mixture was stirred at room temperature overnight and quenched with water, extracted with ether to produce about 88% of the desired alcohol. 3-(Trifluoromethyl)phenyl-1-propanol was obtained in about 72% yield using this procedure. A solution of the alcohol (0.1 mol) and $PBr_3$ in 100 ml of chloroform then was stirred at room temperature overnight, and poured into water (100 ml). The organic phase was washed with water (2×10 ml), dried and evaporated to produce the corresponding bromide. In accordance with this method, 2-bromo-1-phenylpropanes were prepared; 2-Bromo-1-(3-chlorophenyl)propane was obtained as a colorless oil with a yield of about 51%, and 2-Bromo-1-(3-trifluoromethyl)phenylpropane was obtained as a colorless oil with a yield of about 42%.

These products were alkylated to produce the compound 1 above. A solution of 1-(diphenyl)methylpiperazine (0.1 mol), 2-bromo-1-phenylpropane (commercially available, 0.11 mol) and triethylamine (0.2 ml) in 20 ml DMF was refluxed for about 4 hours. The mixture was evaporated to dryness in vacuum. The residue was passed through silica gel column to produce compound 1 as a colorless liquid, which then was converted to its hydrochloride salt having a melting point within the range of 244–246° C. The final product (hydrochloride salt thereof) was a white solid having a molecular weight of about 435.9.

2. Synthesis of compounds of formula (II)

Preparation of 1,2-Bis(diphenylmethoxy)ethane and 2-Diphenylmethoxyethanol

Compound 2; 1,2-Bis(diphenylmethoxy)ethane was prepared in accordance with the general pathway outlined above for preparation of compounds of Formula (II). Compound 3; 2-Diphenylmethoxyethanol is a by-product of that pathway synthesis, and can be used in other pathways to produce other compounds useful in the present invention.

Compound 2

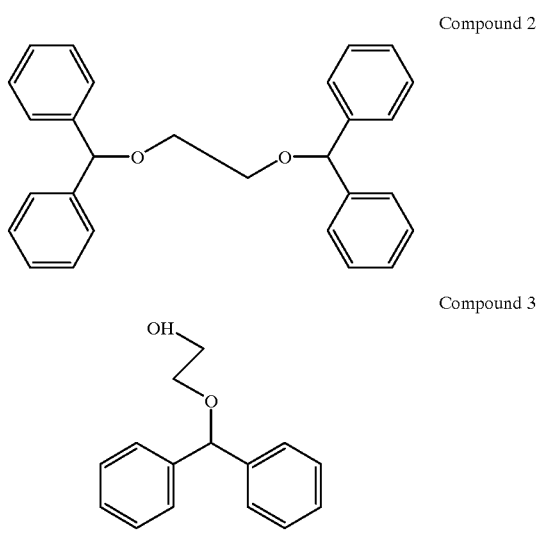

Compound 3

Compound 4

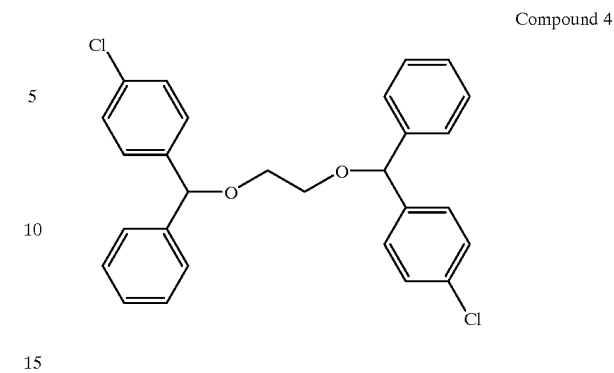

In accordance with the pathway synthesis for making compounds of Formula (II), benzhydryl bromide (19 g, 0.077 mol) and ethylene glycol (27.8 g in 25 ml; 0.45 mol) were combined and stirred. Nitrogen ws bubbled through the reaction. The mixture was warmed on a steam bath. As the mixture warmed, the benzhydryl bromide melted and formed a layer denser than the ethylene glycol. As the reaction proceeded, the layer became less dense than ethylene glycol. The reaction appeared to be complete after 10 minutes and TLC (methylene chloride) confirmed that the reaction was complete. The diether, compound 2, had an $R_f$ of 0.6. Benzhydryl bromide reacted almost instantly with alcohols.

The reaction then was cooled to room temperature and then was diluted with 100 ml of water and extracted with 2×50 ml of methylene chloride. The methylene chloride solution was filtered through IPS filter paper and stripped. The resulting material (14 g) was then flash column chromatographed on 150 g of flash chromatography silica gel. After crystallization from hexane, compound 2 formed a white crystalline solid having a melting point within the range of from about 99–103° C., and a molecular weight of 394.5, and compound 3 formed a white crystalline solid having a melting point within the range of from about 68–70° C. and a molecular weight of about 228.3.

Preparation of 1,2-Bis(4-chlorophenylphenylmethoxy)ethane

The general pathway for producing compounds such as compound 2, with various substituents X (X can be $CH_3$, $OCH_3$, $CF_3$, Cl, Br and other halogens, C1–C5 alkyl, etc.) is outlined above. Compound 4 below, where X is Cl was prepared in accordance with the aforementioned general pathway.

In accordance with the pathway synthesis for making compounds of Formula (II), benzhydrol (8.7 g, 0.044 mol) and ethylene glycol (33 g in 30 ml; 0.53 mol) were combined and warmed on a steam bath. Once the solution was complete, methane sulfonic acid (2 ml, 0.03 mol) was added and the reaction mixture immediately became cloudy. The TLC (methylene chloride) indicated that the reaction was complete on mixing. Compound 4 had an $R_f$ of 0.7. The reaction then was cooled to room temperature and diluted with 100 ml of water and extracted with 2×50 ml of methylene chloride. The methylene chloride solution was filtered through IPS filter paper and stripped.

The resulting material then was flash chromatographed on 100 g of flash chromatography silica gel. Compound 4 was crystallized from hexane and formed a liquid at room temperature, and had a molecular weight of 463.4.

Preparation of 1,2-Bis(4-trifluoromethylphenyl phenylmethoxy)ethane

A procedure identical to that above was used only X for compound 5 below was $CF_3$ instead of Cl.

Compound 5

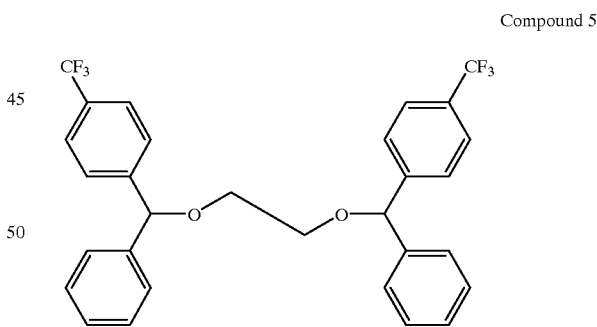

Compound 5, like compound 4 above, was crystallized from hexane and formed a liquid at room temperature and had a molecular weight of 530.5.

Preparation of 1,2-Bis(2-methylphenyl phenylmethoxy)ethane

A procedure identical to that above was used only X for compound 6 below was $CH_3$ instead of Cl or $CF_3$.

Compound 6

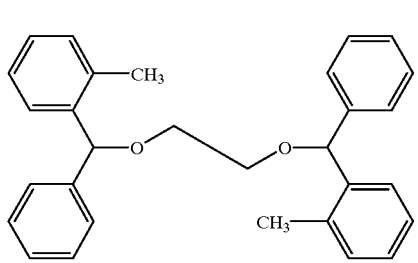

Compound 6, like compounds 4 and 5 above, was crystallized from hexane and formed a solid crystalline material having a melting point within the range of from about 105–109° C., and had a molecular weight of 422.6.

Preparation of 1,2-Bis(3-methylphenyl phenylmethoxy)ethane

A procedure substantially like that above was used; only X for compound 7 below, however, was $CH_3$ instead of Cl or $CF_3$.

Compound 7

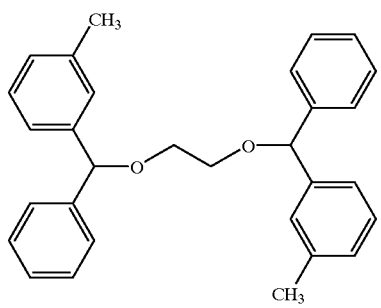

Compound 7, like compounds 4–6 above, was crystallized from hexane and formed a liquid oily substance having a molecular weight of 422.6.

Preparation of 1,2-Bis(4-methylphenyl phenylmethoxy)ethane

A procedure identical to that above was used only X for compound 8 below was $CH_3$ instead of Cl or $CF_3$.

Compound 8

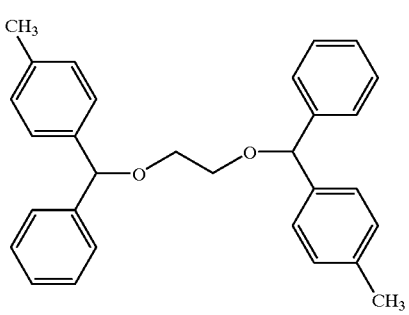

Compound 8, like compounds 4–7 above, was crystallized from hexane and formed a white crystalline solid material having a melting point in the range of from about 107–116° C., and had a molecular weight of 422.6.

3. Synthesis of compounds of formula (III)

Preparation of 3-(10,11-Dihydro-5H-dibenzo[a,d]cyclohepten-5-ylidene-N-methyl-N-[2-(diphenylmethoxy)ethyl)]-1-propaneamine The general pathway for synthesizing compounds of formula (III) is outlined above. Compound 9 below was prepared in accordance with that general pathway.

Compound 9

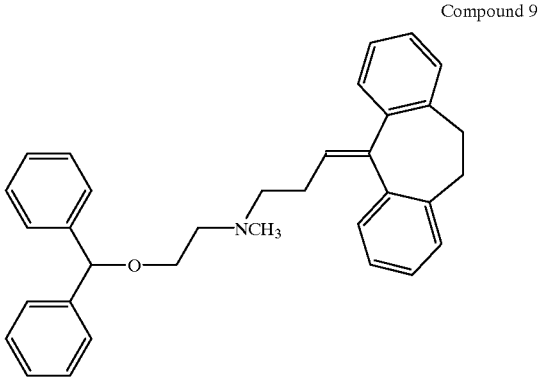

Compound 9 was prepared by first preparing compound 3 above, 2-diphenylmethoxyethanol, (0.54 g, 0.003 mol) and then treating equimolar amounts (0.045 mol) with tosyl chloride (0.6 g, 0.045 mol) in 30 ml dichloromethane and 15 ml pyridine, and stirred overnight at room temperature. The mixture was extracted with dichloromethane and was added to a methylene chloride solution of 3-(10,11-Dihydro-5H-dibenzo[a,d]cyclohepten-5-ylidine-N-methyl)-1-propanamine (nortryptylene; 0.79 g, 0.002 mol). This mixture then was stirred at room temperature for 24 hours and then neutralized and purified by chromatography to produce compound 9, which was subsequently formed into its fumaric acid salt. The salt of compound was a tan powder having a molecular weight of about 589.7, whereby the molecular weight of compound 9 was 473.7.

Preparation of 3-(10,11-Dihydro-5H-dibenzo[a,d]cyclohepten-5-ylidene-N-methyl-N-[2-(4-chlorophenyl phenylmethoxy)ethyl)]-1-propaneamine A procedure identical to that above was used, except that, for compound 10, one of the diphenyl moieties in compound 9 above was substituted with a chlorine.

Compound 10

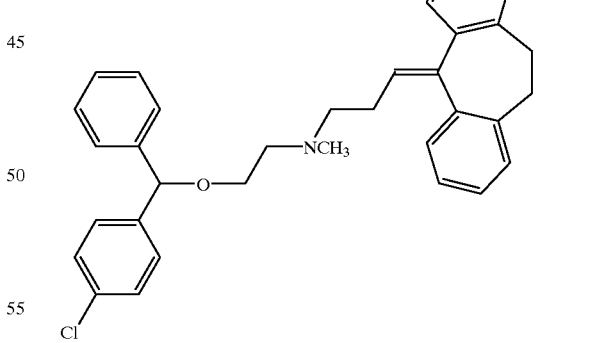

Compound 10, like compound 9 above, was formed into its fumaric acid salt which produced a hygroscopic, light-sensitive tan foam product having a molecular weight of 624.2, whereby compound 10 had a molecular weight of 508.1.

4. Synthesis of compounds of formula (IV)

Compound 11 below was prepared in accordance with the general pathway outlined above for preparing compounds of Formula (IV).

Compound 11

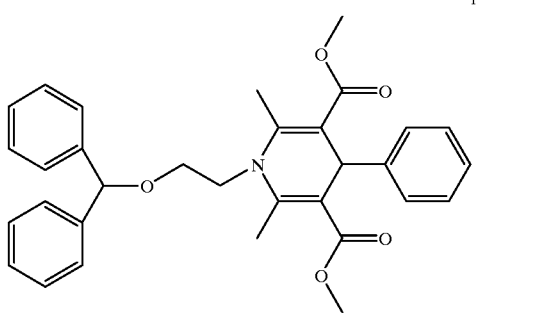

5. Synthesis of compounds of formula (V)
Preparation of 2-[4-(1,2-Diphenylethynyl)phenoxy]-diphenylmethylpiprazine Compound 12 below was prepared in accordance with the general pathway outlined above for preparing compounds of Formula (V):

Compound 12

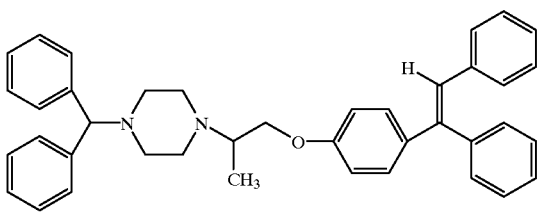

Compound 12 was prepared in accordance with the pathway synthesis described above for preparing compounds of general formula (V). In accordance with this synthesis pathway. About 98 ml or a 0.2M solution of the grignard reagent, benzyl magnesium chloride in THF (0.196 mol), was added to a 1000 ml flask equipped with thermometer and dropping funnel, whereby the flask was charged with about 38 grams of 4-methoxybenzophenone (0.179 mole in 400 ml THF). The grignard reagent was rapidly added while maintaining the temperature below 20° C. with an ice bath under a nitrogen atmosphere. The ice bath then was removed and the reactants heated to 40° C., was stirred for about 1 hour, poured into about 1 L of cold 10% HCl and extracted with about 350 ml of ethyl acetate. This produced a yello-green oil, after concentration in vacuo, which subseqently was treated with 2 L of boiling hexanes and the boiling solution was filtered through a plug of glass wool. The solution then was concentrated to a volume of about 700 ml and set aside to cool. After cooling, the solution was filtered, washed and air dried to yield a crystalline material.

Approximately 26 g of the crystalline material was mixed in a 500 ml flask with about 26 g of boric acid and slowly heated to 250° C. under nitrogen. The temperature was maintained for 10 minutes, the reactants then were allowed to cool to room temperature and 350 ml of water was added. After boiling to dissolve any inorganics, the mixture was cooled to room temperature, extracted with toluene and washed twice with water. The intermediate product was filtered through a plug of silica to yield 18.5 g of pure material after combining fractions and concentrating.

About 12 grams of the intermediate product (0.042 mol) was mixed with about 51 g of NaCN and 75 ml of DMSO and magnetically stirred while heating at 160–170° C. under nitrogen for about 6 hours. Heating was discontinued overnight, and resumed for 8 hours the remaining day. Again, heating was discontinued overnight, and resumed for 4 hours the remaining day. After heating, the reaction mixture was diluted with 1.5 L of water and transferred to a 2 L separation funnel. The mixture was acidified to pH 2 with concentrated HCl and extracted with 3×300 ml toluene. The combined toluene extract was back extracted twice with 300 ml of water, dried over sodium sulfate, nitrogen bubbled through the solution to displace HCN, filtered and concentrated in vacuo to yield about 12.06 g of a dark brown phenolic material.

About 2 grams of the dark brown phenolic material (7.34 mmol) was charged with 20 ml THF to a pressure vessel and about 4.0 ml of 2.5 mmolar n-BuLi (10 mmol) were added under a blanket of nitrogen. The vessel was sealed and cooled to −78° C., the top removed and about 3 g of propylene oxide (51.65 mmol) was added. The vessel then was sealed with parafilm and allowed to warm to room temperature. Upon reaching room temperature, the vessel was sealed with a Teflon top and placed in a water bath at 55–60° C. After 5 days, the temperature was increased to 80° C. and maintained there for 14 days.

After 14 days at 80° C., the reaction (now about 75% complete) was diluted with water, acidified with concentrated HCl and extracted 3 times with ethyl acetate. The combined extracts were back extracted twice with water, the organic layer dried, filtered and concentrated to yield 3.14 g of a crude reaction mixture. the mixture then was dissolved in dichloromethane and introduced onto a 5×12 cm column of silica and eluted first with EtAc/hexane 10/90 and then 15/85. Unreacted starting material eluted quickly and the products were eluted as an elongated spot by TLC. Multiple elutions with 7/93 EtAc/hexane resolved the mixture into two component mixtures, each containing E and Z isomers. After a series of acetylation and elutions, fractions containing about 1.17 g of a secondary alcohol product was obtained.

This secondary alcohol (910 mg, 2.75 mmol) was mixed together with 760 mg of Tosyl chloride (4.0 mmol) and 5 ml of pyridine, and magnetically stirred overnight in a 25 ml flask. An additional 320 mg of tosyl chloride then was added after 25 hours and stirring was continued for an additional 24 hours. Upon completion of the reaction, the solution was diluted to 500 ml with water, extracted with 200 ml of ethyl acetate and the ethyl acetate washed twice with water, once with 10% HCl and twice with water. The ethyl acetate was concentrated in vacuo to yield about 1.35 g of a syrup, which subsequently was introduced onto a 25×500 mm MPLC column dissolved in dichloromethane and the column eluted with EtAc/hexanes 10/90. About 1.21 grams of a tosylated product were obtained.

About 905 mg of the tosylated product in 20 ml of o-xylene was added to a 100 ml 3 necked flask. Meanwhile, a 50 ml flask as charged with about 1420 mg of diphenyl-methylpiperazine (5.6 mmol) and 2.24 ml of 2.5 mmolar n-BuLi (5.6 mmol), both in 20 ml of o-xylene, was added under nitrogen at room temperature. The solution was maintained for 30 minutes at room temperature and then added to the 3 necked flask containing the tosylated product. The reaction was refluxed for 4 hours, the heat was removed and stirred overnight at room temperature. Refluxing was continued an additional hour.

The reaction was cooled to room temperature, transferred to a 125 ml separation funnel, the flask rinsed with toluene and combined with the original solution and extracted three times with 2ml portions of water. The o-xylene/toluene solution was dried over sodium sulfate, the solution filtered and concentrated in vacuo to yield 2 grams of a thick red syrup. The syrup then was dissolved in dichloromethane and filtered through a 5×10 cm plug of silica gel eluting with EtAc/hexanes 30/70. Fractions were combined and concentrated to yield about 326 mg of a red syrup. This syrup then was introduced onto a 15×500 mm MPLC column in dichloromethane and the column was eluted with EtAc/hexanes 20/80. Fractions again were combined and concentrated to yield about 200 mg of compound 12 which was present as a tan to brown syrup.

6. Synthesis of compounds of formula (VI)

Preparation of 3,7-Dimethyl-5-[2-(diphenylmethoxy)-ethyl] xanthine

Compound 13 below was prepared using the general pathway synthesis above for preparing compounds of Formula (VI).

Compound 13

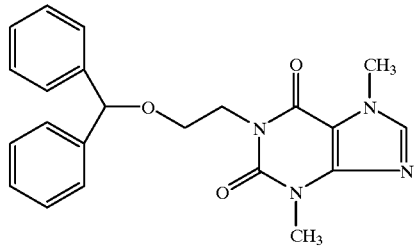

Compound 13 was prepared by preparing a solution of theobromine, (0.54 g, 0.003 mol), potassium t-butoxide (0.833 g, 0.002 mol) and sodium hydroxide (0.24 g, 0.006 mol) in 100 ml methanol, and stirring under nitrogen for about two hours. The tosylate of compound number 3 (2-diphenylmethoxyethanol) was formed in accordance with the general synthesis of formula (III) compounds and added to the mixture. The reaction mixture was stirred at room temperature for about 24 hours, and the mixture was neutralized with hydrochloric acid (about 20 ml, 1N solution). The neutralized mixture then was purified by flash chromatography to produce about 25% of compound 13, which was a white crystalline material having a melting point within the range of from about 114–116°c., and a molecular weight of about 390.1.

Preparation of 3,7-Dimethyl-5-[2-(4-chlorophenyl phenylmethoxy)-ethyl]xanthine

Compound 14 below was prepared using the same procedure as described above for compound 13, except the chlorinated derivative of compound 3 was used instead of compound 3.

Compound 14

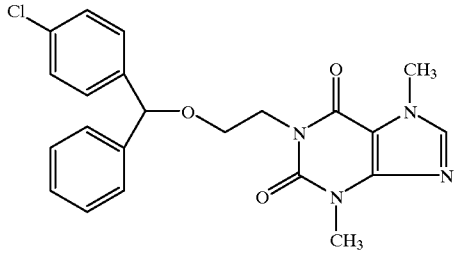

The procedure for preparing compound 13 was repeated, except that the theobromine solution was mixed with a chlorinated tosylate derivative of compound 3. The reaction mixture was stirred at room temperature for about 24 hours, and the mixture was neutralized with HCl (about 20 ml, 1N solution). The neutralized mixture then was purified by flash chromatography to produce compound 14, which was a hygroscopic white foam having a molecular weight of about 424.9.

EXAMPLE 5

This example illustrates the effectiveness of a number of compounds of each of formula (I)–(VI) in reducing the number, quantity, and/or volume of disrupted DMS. This example illustrates the effectiveness of a number of compounds in: (i) reducing mean volume of tissue occupied by the disrupted DMS; (ii) reducing the ratio of the number of inflammatory cells per DMS; or (iii) increasing the ratio of the number of macrophages containing disrupted DMS material per DMS. This example therefore illustrates the effectiveness of the inventive compounds in reducing the exponential DMS disruption autocatalytic phenomenon and hence, in reducing the cerebral amyloid burden and formation of amyloid plaque.

1. In vivo testing of compounds of formula (I)–(VI)

The compounds described above in Example 4 were tested in accordance with Example 2. In the following examples, the data of which is reported separately below in Tables I–VII, each of the compounds was administered to four (4) rates in sterile physiological saline containing about 100,000 human DMS and about 50 µl of the compound at $10^{-5}$ M concentration, for a total volume of about 100 µl. Controls were used whereby the control groups were comprised of: (i) four (4) rats that did not receive any injection of DMS or the compound; (ii) four (4) rats that received an injection of DMS and no compound; and (iii) two (2) rats that received an injection of DMS and a compound found to be inactive in Example 2 above. The inactive compounds are listed below as control compounds 1–26, and the results are formulated in Tables I–VII below.

Inactive Control Compounds

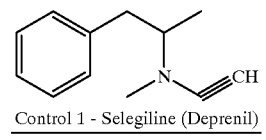

Control 1 - Selegiline (Deprenil)

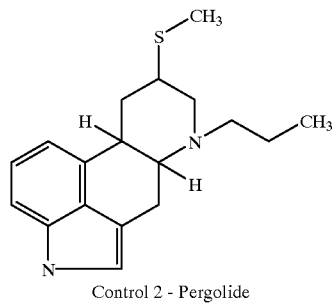

Control 2 - Pergolide

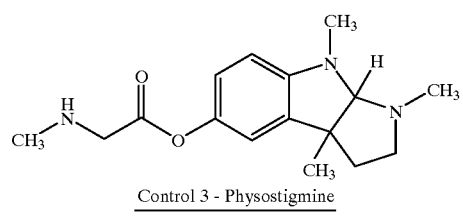

Control 3 - Physostigmine

-continued
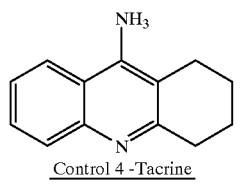
Control 4 - Tacrine
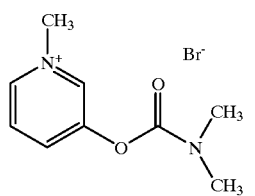
Control 5 - Pyridostigmine Bromide
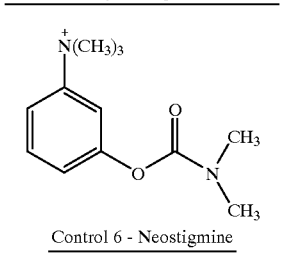
Control 6 - Neostigmine
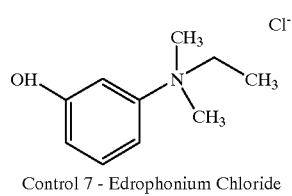
Control 7 - Edrophonium Chloride
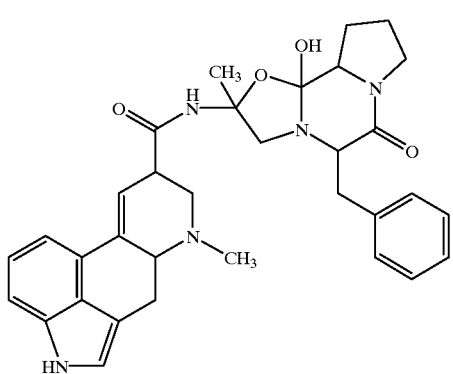
Control 9 - Ergotamine
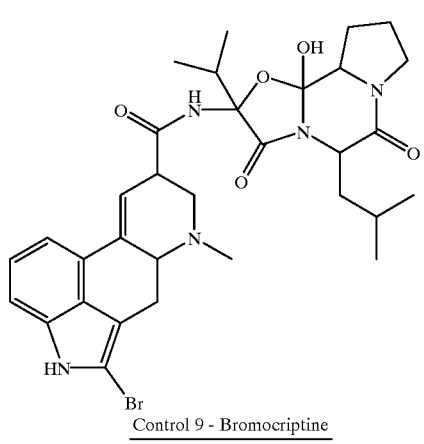
Control 9 - Bromocriptine
-continued
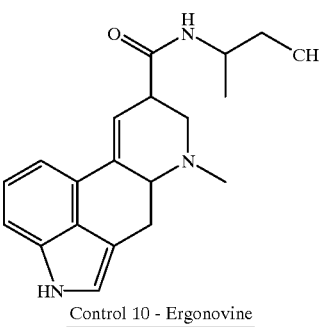
Control 10 - Ergonovine
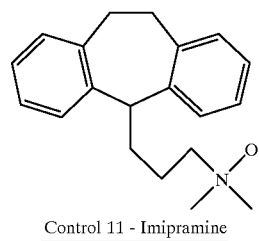
Control 11 - Imipramine
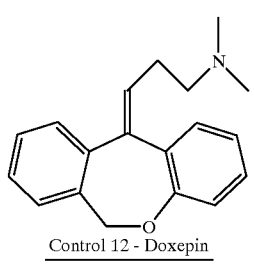
Control 12 - Doxepin
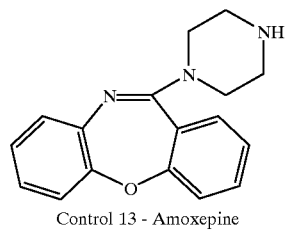
Control 13 - Amoxepine
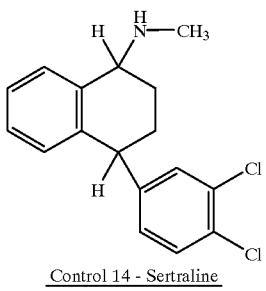
Control 14 - Sertraline
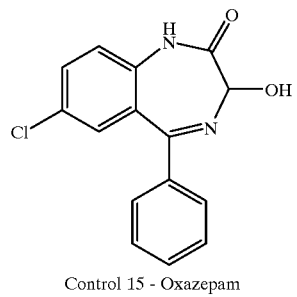
Control 15 - Oxazepam

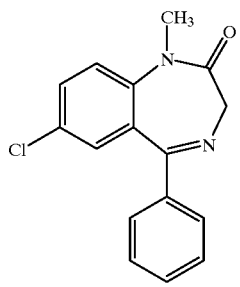

Control 16 - Diazepam (Valium)

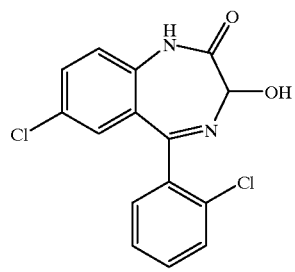

Control 17 - Lorazepam

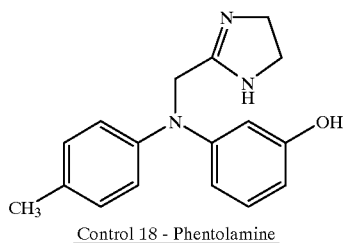

Control 18 - Phentolamine

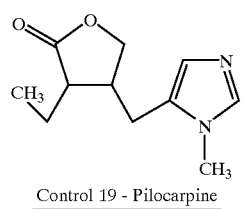

Control 19 - Pilocarpine

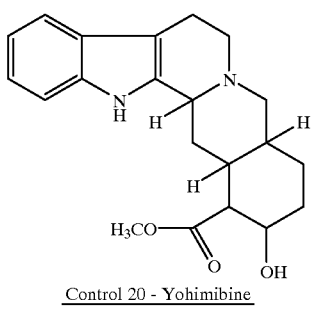

Control 20 - Yohimibine

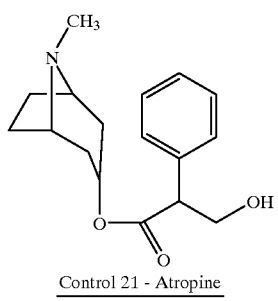

Control 21 - Atropine

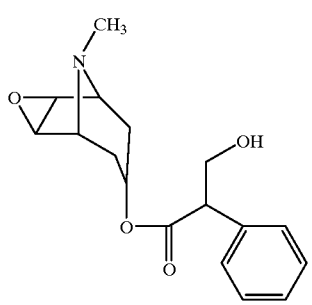

Control 22 - Scopolamine

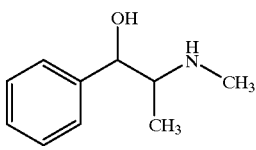

Control 23 - Ephedrine

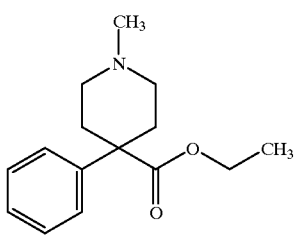

Control 24 - Meperidine

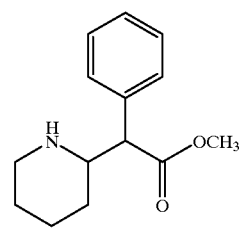

Control 25 - Methylphenidate

The following tables summarizes the data obtained in accordance with this example. In the tables, the various compounds of the present invention were tested against: control (i), animals that did not receive any injection of DMS or either compounds of the invention or control compounds; control (ii), animals that received an injection of DMS and no compound; and control (iii), animals that received an injection of DMS and an inactive control compound. The initial mean volume of tissue occupied by the DMS, the mean volume of tissue occupied by disrupted DMS, the ratio of the number of inflammatory cells per DMS (i.e., persistence of inflammatory reaction) and the ratio of the number of macrophages containing disrupted DMS material (i.e, digestion and removal of DMS) were measured and tabulated.

1. Compounds of Formula (I)

TABLE I

| Compound | Mean Volume DMS ($\mu^3$) | Mean Volume Disrupted DMS[1] ($\mu^3$) | Persistence of Inflamm. Reaction[2] | Digestion and removal of DMS[3] |
| --- | --- | --- | --- | --- |
| 1 | 1153 | 1250 | <0.01 | >10 |
| Cont. (i) | 1153 | 0 | 0 | 0 |
| Cont. (ii) | 1153 | $1.7 \times 10^5$ | 1.0 | 1.0 |
| Atropine | 1153 | $1.8 \times 10^5$ | 1.0 | 1.0 |
| Scopolamine | 1153 | $1.8 \times 10^5$ | 1.0 | 1.0 |
| Meperidine | 1153 | $2.1 \times 10^5$ | 1.0 | 1.0 |

[1]- denotes the mean tissue volume of transformed redistributed disrupted DMS protein per individual DMS;
[2]- denotes persistence of inflammatory reaction at DMS disruption site: ratio of number of acute inflammatory cells (excluding macrophages) per DMS at the DMS disruption site, compared to control (ii), the latter normalized to 1.0; and
[3]- denotes evidence of digestion and removal of DMS material by reticuloendothelial system: ratio of number of macrophages containing intact or digested, altered, proteolyzed or otherwise transformed DMS per DMS at the DMS disruption site, compared to control (ii), the latter normalized to 1.0.

2. Compounds of Formula (II)

TABLE II

| Compound | Mean Volume DMS ($\mu^3$) | Mean Volume Disrupted DMS ($\mu^3$) | Persistence of Inflamm. Reaction | Digestion and removal of DMS |
| --- | --- | --- | --- | --- |
| 2 | 525 | 560 | <0.01 | >10 |
| 4 | 525 | 580 | <0.01 | >10 |
| Cont. (i) | 0 | 0 | 0 | 0 |
| Cont. (ii) | 525 | $1.5 \times 10^5$ | 1.0 | 1.0 |
| Physostigmine | 525 | $1.1 \times 10^5$ | 1.0 | 1.0 |
| Pyridostigmine bromide | 525 | $1.5 \times 10^5$ | 1.1 | 1.0 |
| Tacrine | 525 | $1.4 \times 10^5$ | 1.1 | 1.0 |

TABLE III

| Compound | Mean Volume DMS ($\mu^3$) | Mean Volume Disrupted DMS ($\mu^3$) | Persistence of Inflamm. Reaction | Digestion and removal of DMS |
| --- | --- | --- | --- | --- |
| 5 | 907 | 940 | <0.01 | >10 |
| 6 | 907 | 940 | <0.01 | >10 |
| Cont. (i) | 0 | 0 | 0 | 0 |
| Cont. (ii) | 907 | $1.05 \times 10^5$ | 1.0 | 1.0 |
| Pergolide | 907 | $1.2 \times 10^5$ | 1.1 | 1.0 |
| Bromocriptine | 907 | $1.04 \times 10^5$ | 1.0 | 1.0 |
| Selegiline | 907 | $1.3 \times 10^5$ | 1.0 | 1.0 |

3. Compounds of Formula (III)

TABLE IV

| Compound | Mean Volume DMS ($\mu^3$) | Mean Volume Disrupted DMS ($\mu^3$) | Persistence of Inflamm. Reaction | Digestion and removal of DMS |
| --- | --- | --- | --- | --- |
| 9 | 383 | 482 | <0.01 | >10 |
| 10 | 383 | 460 | <0.01 | >10 |
| Cont. (i) | 0 | 0 | 0 | 0 |
| Cont. (ii) | 383 | $7.3 \times 10^4$ | 1.0 | 1.0 |
| Diazepam | 383 | $6.5 \times 10^4$ | 1.1 | 1.0 |
| Oxazepam | 383 | $6.8 \times 10^4$ | 1.1 | 1.0 |
| Lorazepam | 383 | $8.2 \times 10^4$ | 1.1 | 1.0 |

4. Compounds of Formula (IV)

TABLE V

| Compound | Mean Volume DMS ($\mu^3$) | Mean Volume Disrupted DMS ($\mu^3$) | Persistence of Inflamm. Reaction | Digestion and removal of DMS |
| --- | --- | --- | --- | --- |
| 11 | 907 | 1260 | <0.01 | >10 |
| Cont. (i) | 0 | 0 | 0 | 0 |
| Cont. (ii) | 907 | $1.02 \times 10^5$ | 1.0 | 1.0 |
| Imipramine | 907 | $1.38 \times 10^5$ | 1.0 | 1.0 |
| Sertraline | 907 | $1.22 \times 10^5$ | 1.1 | 1.0 |
| Amoxepine | 907 | $1.36 \times 10^5$ | 1.1 | 1.0 |

5. Compounds of Formula (V)

TABLE VI

| Compound | Mean Volume DMS ($\mu^3$) | Mean Volume Disrupted DMS ($\mu^3$) | Persistence of Inflamm. Reaction | Digestion and removal of DMS |
| --- | --- | --- | --- | --- |
| 12 | 525 | 740 | <0.01 | >10 |
| Cont. (i) | 0 | 0 | 0 | 0 |
| Cont. (ii) | 525 | $5.1 \times 10^4$ | 1.0 | 1.0 |
| Ergotamine | 525 | $5.8 \times 10^4$ | 1.0 | 1.0 |
| Ergonovine | 525 | $5.2 \times 10^4$ | 1.0 | 1.0 |
| Methylphenidate | 525 | $5.8 \times 10^4$ | 1.1 | 1.01 |

6. Compounds of Formula (VI)

TABLE VII

| Compound | Mean Volume DMS ($\mu^3$) | Mean Volume Disrupted DMS ($\mu^3$) | Persistence of Inflamm. Reaction | Digestion and removal of DMS |
| --- | --- | --- | --- | --- |
| 13 | 1440 | 1625 | <0.01 | >10 |
| 14 | 1440 | 1625 | <0.01 | >10 |
| Cont. (i) | 0 | 0 | 0 | 0 |
| Cont. (ii) | 1440 | $1.7 \times 10^5$ | 1.0 | 1.0 |
| Neostigmine | 1440 | $1.4 \times 10^5$ | 1.1 | 1.0 |
| Edrophonium Chloride | 1440 | $2.2 \times 10^5$ | 1.0 | 1.0 |
| Pilocarpine | 1440 | $1.7 \times 10^5$ | 1.1 | 1.0 |

As can be seen from the table above, the compounds of the present invention reduced the mean tissue volume of disrupted DMS and associated injury foci in vivo by at least 10% when compared to control groups (ii) and (iii). As can also be seen in the table above, the compounds of the present invention furthermore reduced the ratio of the number of inflammatory cells per DMS at the DMS disruption site by at least 10% when compared to control groups (ii) and (iii). In addition, as can be seen from the table above, the compounds of the present invention furthermore increased the ratio of the number of macrophages containing disrupted DMS material at the DMS disruption site by greater than 10% when compared to control groups (ii) and (iii).

The present invention has been described by reference to the particularly preferred embodiments and examples above. Those skilled in the art will appreciate that various modifications can be made to the invention without departing significantly from the spirit and scope thereof.

What is claimed is:

1. A composition for treating cerebral amyloidosis, comprising a pharmaceutically effective amount of:
   (i) a compound that impedes disruption of intact dense microspheres (DMS) by acting on DMS either to (a) prevent disruption, or (b) if disrupted, act on pre-disrupted DMS in such a way that the compound, when compared to controls:
      (1) reduces the mean volume of tissue occupied by disrupted DMS;
      (2) reduces the ratio of the number of inflammatory cells per DMS; or
      (3) increases the ratio of the number of macrophages containing disrupted DMS per DMS;
   when the compound is administered to a test animal that has received an injection of DMS, and
   (ii) a pharmaceutically acceptable vehicle,
   wherein the compound is represented by the following general Formula (I):

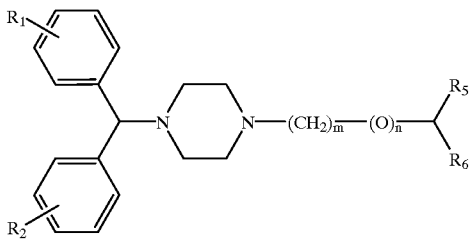

Formula (I)

wherein:
   $R_1$ and $R_2$ each are one or more independent substituents selected from the group consisting of hydrogen, C1–C5 alkyl, C2–C5 alkenyl, C3–C5 cycloalkyl, C2–C5 alkynyl, nitro, and halogen;
   $R_5$ and $R_6$ are independently selected from the group consisting of C1–C5 alkyl, C2–C5 alkenyl, C3–C5 cycloalkyl, C2–C5 alkynyl, phenyl, benzyl, naphthyl, and anthracenyl;
   wherein each aromatic ring may be substituted by one or more substituents selected from the group consisting of halogen, C1–C5 alkyl, C2–C5 alkenyl, C2–C5 alkynyl, and C1–C5 haloalkyl;
   m is an integer selected from the group consisting of 0, 1, 3, 4, and 5;
   n is 1; or
a pharmaceutically acceptable salt of such compound.

2. A composition as claimed in claim 1, wherein the composition displays an adequate ability to traverse the blood-brain barrier.

3. A composition as claimed in claim 1, whereby the compound prevents the DMS from disrupting.

4. A composition as claimed in claim 1, whereby the compound impedes disruption of intact DMS by acting on DMS prior to disruption in such a way that when disrupted, the compounds, when compared to controls:
   (1) reduce the mean volume of tissue occupied by disrupted DMS;
   (2) reduce the ratio of the number of inflammatory cells per DMS; or
   (3) increase the ratio of the number of macrophages containing disrupted DMS per DMS.

5. A method for treating cerebral amyloidosis, comprising the step of administering to a subject, in whom disruption of intact DMS is anticipated, a pharmaceutically effective amount of a composition according to claim 1.

6. A method as claimed in claim 5, wherein the composition displays an adequate ability to traverse the blood-brain barrier.

7. A method as claimed in claim 5, whereby said method prevents the DMS from disrupting.

8. A method as claimed in claim 5, whereby said method impedes disruption of intact DMS by acting on DMS prior to disruption in such a way that when disrupted, the compounds, when compared to controls:
   (1) reduce the mean volume of tissue occupied by disrupted DMS;
   (2) reduce the ratio of the number of inflammatory cells per DMS; or
   (3) increase the ratio of the number of macrophages containing disrupted DMS per DMS.

9. A compound represented by the following general Formula (I):

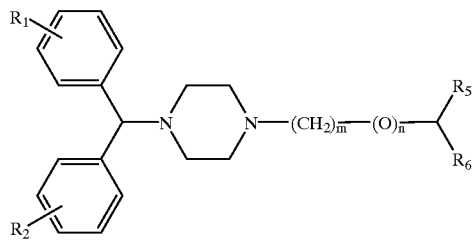

$R_1$ and $R_2$ each are one or more independent substituents selected from the group consisting of hydrogen, C1–C5 alkyl, C2–C5 alkenyl, C3–C5 cycloalkyl, C2–C5 alkynyl, nitro, and halogen;

$R_5$ and $R_6$ are independently selected from the group consisting of C1–C5 alkyl, C2–C5 alkenyl, C3–C5 cycloalkyl, C2–C5 alkynyl, phenyl, benzyl, naphthyl, and anthracenyl;

wherein each aromatic ring may be substituted by one or more substituents selected from the group consisting of halogen, C1–C5 alkyl, C2–C5 alkenyl, C2–C5 alkynyl, and C1–C5 haloalkyl;

m is an integer selected from the group consisting of 0, 1, 3, 4, and 5; and n is 1; or a pharmaceutically acceptable salt of such compound.

* * * * *